(12) United States Patent
Fu

(10) Patent No.: US 11,841,363 B2
(45) Date of Patent: Dec. 12, 2023

(54) ZNT8 ASSAYS FOR DRUG DEVELOPMENT AND PHARMACEUTICAL COMPOSITIONS

(71) Applicant: THE JOHNS HOPKINS UNIVERSITY, Baltimore, MD (US)

(72) Inventor: Dax Fu, Short Hills, NJ (US)

(73) Assignee: The Johns Hopkins University, Baltimore, MD (US)

( * ) Notice: Subject to any disclaimer, the term of this patent is extended or adjusted under 35 U.S.C. 154(b) by 288 days.

(21) Appl. No.: 17/242,938

(22) Filed: Apr. 28, 2021

(65) Prior Publication Data
US 2021/0263021 A1  Aug. 26, 2021

Related U.S. Application Data

(63) Continuation of application No. 16/095,394, filed as application No. PCT/US2017/029250 on Apr. 25, 2017, now Pat. No. 11,016,085.

(60) Provisional application No. 62/326,871, filed on Apr. 25, 2016.

(51) Int. Cl.
| | |
|---|---|
| A61K 9/127 | (2006.01) |
| A61P 3/10 | (2006.01) |
| A61K 31/56 | (2006.01) |
| G01N 33/543 | (2006.01) |
| G01N 33/574 | (2006.01) |
| A61K 31/6615 | (2006.01) |
| G01N 33/68 | (2006.01) |

(52) U.S. Cl.
CPC ......... *G01N 33/5432* (2013.01); *A61K 9/127* (2013.01); *A61K 31/56* (2013.01); *A61K 31/6615* (2013.01); *A61P 3/10* (2018.01); *G01N 33/57407* (2013.01); *G01N 33/57434* (2013.01); *G01N 33/6893* (2013.01); *G01N 2800/042* (2013.01)

(58) Field of Classification Search
CPC ........... A61P 3/10; A61K 9/127; A61K 31/56; A61K 31/6615; C01N 33/5432; C01N 33/57407; C01N 33/57434; C01N 33/6893; C01N 2800/42
USPC ........................................................ 514/136
See application file for complete search history.

(56) References Cited

U.S. PATENT DOCUMENTS

| | | | |
|---|---|---|---|
| 4,399,216 A | 8/1983 | Axel et al. | |
| 4,634,665 A | 1/1987 | Axel et al. | |
| 4,880,935 A | 11/1989 | Thorpe | |
| 5,122,368 A | 6/1992 | Greenfield et al. | |
| 5,179,017 A | 1/1993 | Axel et al. | |
| 5,225,539 A | 7/1993 | Winter | |
| 5,399,363 A | 3/1995 | Liversidge et al. | |
| 5,466,468 A | 11/1995 | Andra et al. | |
| 5,530,101 A | 6/1996 | Queen et al. | |
| 5,543,158 A | 8/1996 | Gref et al. | |
| 5,580,579 A | 12/1996 | Ruddy et al. | |
| 5,585,089 A | 12/1996 | Queen et al. | |
| 5,622,929 A | 4/1997 | Willner et al. | |
| 5,624,821 A | 4/1997 | Winter et al. | |
| 5,629,001 A | 5/1997 | Michael et al. | |
| 5,641,515 A | 6/1997 | Ramtoola | |
| 5,641,640 A | 6/1997 | Hanning | |
| 5,725,871 A | 3/1998 | Illum | |
| 5,731,168 A | 3/1998 | Carter et al. | |
| 5,756,353 A | 5/1998 | Debs | |
| 5,780,045 A | 7/1998 | McQuinn et al. | |
| 5,792,451 A | 8/1998 | Sarubbi et al. | |
| 5,804,212 A | 9/1998 | Illum | |
| 5,824,805 A | 10/1998 | King et al. | |
| 5,834,597 A | 11/1998 | Tso et al. | |
| 5,859,205 A | 1/1999 | Adair et al. | |
| 5,869,046 A | 2/1999 | Presta et al. | |
| 5,892,019 A | 4/1999 | Schlom et al. | |
| 6,165,710 A | 12/2000 | Robinson | |
| 6,214,345 B1 | 4/2001 | Firestone et al. | |
| 6,407,213 B1 | 6/2002 | Carter et al. | |
| 6,613,308 B2 | 9/2003 | Bartus et al. | |
| 6,737,514 B1 | 5/2004 | Wang | |
| 6,881,557 B2 | 4/2005 | Foote | |
| 8,563,291 B2 | 10/2013 | Yoshimura et al. | |
| 9,568,482 B2 | 2/2017 | Seve et al. | |
| 11,016,085 B2 | 5/2021 | Fu | |
| 2009/0186364 A1 | 7/2009 | Yoshimura et al. | |
| 2009/0191574 A1 | 7/2009 | Halperin | |
| 2010/0068199 A1 | 3/2010 | Liang | |
| 2010/0158909 A1 | 6/2010 | McDonagh et al. | |
| 2012/0238572 A1 | 9/2012 | Su et al. | |
| 2016/0025744 A1 | 1/2016 | Feldman et al. | |
| 2017/0096497 A1 | 4/2017 | Weisbart | |
| 2018/0243408 A1 | 8/2018 | Fanger et al. | |
| 2019/0137485 A1 | 5/2019 | Fu | |

(Continued)

FOREIGN PATENT DOCUMENTS

| | | |
|---|---|---|
| CN | 101646781 | 2/2010 |
| CN | 106084043 | 11/2016 |
| CN | 106084051 | 11/2016 |

(Continued)

OTHER PUBLICATIONS

Wenzlau et al PNAS, 2007, 104(43) 17040-17045 (Year: 2007).*

(Continued)

*Primary Examiner* — Yevgeny Valenrod

(74) *Attorney, Agent, or Firm* — Fish & Richardson P.C.

(57) ABSTRACT

The present invention describes methods of identifying drugs for the treatment or prevention of diabetes by measuring the activity of the human zinc transporter ZnT8 and pharmaceutical compositions.

20 Claims, 6 Drawing Sheets

(56) References Cited

U.S. PATENT DOCUMENTS

2020/0132698 A1    4/2020  Fu et al.

FOREIGN PATENT DOCUMENTS

| CN | 106771233 | 5/2017 |
|---|---|---|
| EP | 404097 | 12/1990 |
| WO | WO 198705330 | 9/1987 |
| WO | WO 198912624 | 12/1989 |
| WO | WO 199311161 | 6/1993 |
| WO | WO 2008083331 | 7/2008 |
| WO | 2012062697 A1 | 5/2012 |
| WO | WO 2012173184 | 12/2012 |
| WO | WO 2013071055 | 5/2013 |
| WO | 2014142517 A1 | 9/2014 |
| WO | WO 2014160175 | 10/2014 |
| WO | WO 2017189483 | 11/2017 |
| WO | WO 2019014044 | 1/2019 |
| WO | WO 2020037174 | 2/2020 |
| WO | WO 2020247920 | 12/2020 |

OTHER PUBLICATIONS

Sladek, et al., A genome-wide association study identifies novel risk loci for type 2 diabetes. (2007) Nature. 445, 881-885.

Chao, et al., Kinetic Study of the Antiport Mechanism of an *Escherichia coli* Zinc Transporter, ZitB*. (2004) J Biol Chem 279, 12043-12050.

Mathiowitz, et al., Biologically erodable microspheres as potential oral drug delivery systems. (1997) Nature; 386(6623):410-4.

Takenaga, et al., Microparticle resins as a potential nasal drug delivery system for insulin. J Control Release (1998) 52: 81-87.

Flannick, et al., Loss-of-function mutations in SLC30A8 protect against type 2 diabetes. Nat Genet (2014); 46: 357-363.

Wenzlau, et al., The cation efflux transporter ZnT8 (Slc30A8) is a major autoantigen in human type 1 diabetes. Proc Natl Acad Sci U S A. (2007); 104: 17040-17045.

Lu, et al., Structure of the zinc transporter YiiP. Science (2007); 317:1746-1748.

Gupta, et al., Visualizing the kinetic power stroke that drives proton-coupled zinc(II) transport. Nature (2014); 512: 101-104.

Davidson, H., et al., "Zinc Transporter 8 (ZNT8) and Beta Cell Function" Trends Endocrinol Metab. Aug. 2014 ; 25(8): 415-424. doi:10.1016/j.tem.2014.03.008.

Yi, B., et al., "Different role of zinc transporter 8 between type 1 diabetes mellitus and type 2 diabetes mellitus" J Diabetes Investig 2016; 7: 459-465, doi: 10.1111/jdi.12441.

Geertsma, E., et al., "Membrane reconstitution of ABC transporters and assays of translocator function" Nature Protocols, 2008, vol. 3 No. 2; pp. 256-266.

Kawasaki, E., "ZnT8 and type 1 diabetes." Endocrine Journal 2012, 59 (7) pp. 531-537.

Abdiche et al., "Determining Kinetics and Affinities of Protein Interactions Using a Parallel Real-time Label-free Biosensor, the Octet," Analytical Biochemistry, 2008, 377:209-217.

Aplin et al., "Preparation, Properties, and Applications of Carbohydrate Conjugates of Proteins and Lipids," CRC Crit. Rev. Biochem., May 1981, 22:259-306.

Arnon et al, "Monoclonal Antibodies For Immunotargeting Of Drugs In Cancer Therapy," Monoclonal Antibodies And Cancer Therapy, 1986, pp. 243-256.

Arvan et al., "Islet autoantigens: structure, function, localization, and regulation," Cold Spring Harb Perspect Med , Aug. 2012, 2(8):a007658.

Barelle et al., "VNARs: An Ancient and Unique Repertoire of Molecules That Deliver Small, Soluble, Stable and High Affinity Binders of Proteins," Antibodies, 2015, 4(3):240-258.

Berge et al., "Pharmaceutical salts," J. Pharm. Sci., Jan. 1977, 66:1-19.

Better et al., "*Escherichia coli* secretion of an active chimeric antibody fragment," Science, May 1988, 240(4855):1041-1043.

Better et al., "Expression of Engineered Antibodies and Antibody Fragments in Microorganisms," Methods in Enzymology, 1989, 178:476-496.

Bindels et al., "mScarlet: a bright monomeric red fluorescent protein for cellular imaging," Nat Methods, 2017, 14:53-56.

Bird et al., "Single chain antibody variable regions," TIBTECH, 1991, 9:132-137.

Bird et al., "Single-Chain Antigen-Binding Proteins," Science, 1988, 242(4877):423-426.

Bloem et al., "The elusive role of B lymphocytes and islet autoantibodies in (human) type 1 diabetes," Diabetologia, 2017, 60(7):1185-1189.

Bonner-Weir et al., "New perspectives on the microvasculature of the islets of Langerhans in the rat," Diabetes, 1982, 31(10):883-889.

Carter et al., "High level *Escherichia coli* expression and production of a bivalent humanized antibody fragment," Biotechnology, 1992, 10(2):163-167.

Chimienti, "Zinc, pancreatic islet cell function and diabetes: new insights into an old story," NutrResRev, 2013, 26(1):1-11.

Cieslak et al., "Role of proinflammatory cytokines of pancreatic islets and prospects of elaboration of new methods for the diabetes treatment," Acta Biochim Pol, 2015, 62(1):15-21.

Co et al., "A humanized antibody specific for the platelet integrin gpIIb/IIIa," J Immunol,, Mar. 15, 1994, 152(6):2968-2976.

Corbin et al., "A Practical Guide to Rodent Islet Isolation and Assessment Revisited," Biol Proced Online, 2021, 23(1):7.

Darling et al., "Kinetic exclusion assay technology: characterization of molecular interactions," Assay and Drug Dev Tech, 2004, 2(6):647-657.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol., 2002, 169:3076-3084.

Dodson et al., "The role of assembly in insulin's biosynthesis," Curr Opin Struct Biol., Apr. 1998, 8:189-194.

Donath et al., "Type 2 diabetes as an inflammatory disease," Nat Rev Immunol, 2011, 11(2):98-107.

Dubowchik et al., "Receptor-mediated and enzyme-dependent targeting of cytotoxic anticancer drugs," Pharm, Therapeutics., Aug. 1999, 83(2):67-123.

Dwivedi et al., "Loss of ZnT8 function protects against diabetes by enhanced insulin secretion," Nat Genet, 2019, 51:1596-1606.

Edge et al., "Deglycosylation of Glycoproteins by Trifluoromethanesulfonic Acid," Anal. Biochem., 1981, 118:131-137.

El-Gohary et al., "Three-dimensional analysis of the islet vasculature," Anat Rec (Hoboken), 2012, 295:1473-1481.

Eriksson et al., "Pancreatic imaging using an antibody fragment targeting the zinc transporter type 8: a direct comparison with radio-iodinated Exendin-4," Acta Diassbetol, 2018, 55:49-57.

Fukuda et al., "Invitro ecolution of single-chain antibodies using mRNA display," Nucleic Acids Res., 2006, 34(19):e127.

Garner, "Na,K-ATPase in the nuclear envelope regulates Na+: K+ gradients in hepatocyte nuclei," J Membr Bio, 2002, 187:97-115.

Ghazalpour et al., "Comparative analysis of proteome and transcriptome variation in mouse," PLoS Genet, 2011, 7:e1001393.

Ghetie et al., "Multiple roles for the major histocompatibility complex class I-related receptor FcRn," Annu. Rev. Immunol., 2000, 18:739-766.

Ghetie t al., "Transcytosis and catabolism of antibody," Immunol. Res., 2002, 25:97-113.

Gu et al., "Novel autoantibodies to the beta-cell surface epitopes of ZnT8 in patients progressing to type-1 diabetes," J Autoimmun, 2021, 122:102677.

Hahn et al., "3D imaging of human organs with micrometer resolution—applied to the endocrine pancreas," Commun Biol, 2021, 4:1063.

Hara et al., "Transgenic mice with green fluorescent protein-labeled pancreatic beta-cells," Am J Physiol Endocrinol Metab, 2003, 284:E177-183.

(56) References Cited

OTHER PUBLICATIONS

Hieter et al., "Evolution of Human Immunoglobulin kappa J region genes," J. Biol. Chem., 1982, 257:1516-1522.
Hinton et al., "Engineered human IgG antibodies with longer serum half-lives in primates," J. Biol. Chem., 2004, 279:6213-6216.
Ho et al., "Site-directed mutagenesis by overlap extension using the polymerase chain reaction," Gene, 1989, 77:51-59.
Holliger et al., "'Diabodies': small bivalent and bispecific antibody fragments," Proc. Natl. Acad. Sci. U S.A., 1993, 90:6444-6448.
Huang et al., "Coupling of Insulin Secretion and Display of a Granule-resident Zinc Transporter ZnT8 on the Surface of Pancreatic Beta Cells," J Biol Chem, 2017, 292(10):4034-4043.
Hudson et al., "High avidity scFv multimers; diabodies and triabodies," J Immunol. Methods, 1999, 231:177-189.
Huston et al., "Protein engineering of antibody binding sites: recovery of specific activity in an anti-digoxin single-chain Fv analogue produced in *Escherichia coli*," Proc. Natl. Acad. Sci. USA., 1988, 85(16):5879-5883.
Ionescu-Tirgoviste et al., "A 3D map of the islet routes throughout the healthy human pancreas," Sci Rep, 2015, 5:14634.
Iwahashi et al., "CDR subsitutions of a humanized monoclonal antibody (CC49): contributions of individual CDRs to antigen binding and immunogenicity," Mol. Immunol., 1999, 36:1079-1091.
Jefferis et al., "Human immunoglobulin allotypes: possible implications for immunogenicity," 2009, MAbs vol. 1 Issue 4:332-328.
Jermutus et al., "Tailoring in vitro evolution for protein affinity or stability," Proc. Natl. Acad. Sci. USA, 2001, 98:75-80.
Johne et al., "Epitope mapping and binding kinetics of monoclonal antibodies studied by real time biospecific interaction analysis using surface plasmon resonance," J. Immunol. Methods, 1993, 160(2):191-198.
Johnson et al., "Anti-tumor activity of CC49-doxorubicin immunoconguates," Anticancer Res. 1995, 15:1387-93.
Kambe et al., "Zinc transporters and their functional integration in mammalian cells," J Biol Chem, 2021, 100320.
Kaufman et al., "Amplification and expression of sequences cotransfected with a modular dihydrofolate reductase complementary dna gene," Mol. Biol., 1982, 159:601 621.
Kim et al., "In situ quantification of pancreatic beta-cell mass in mice," 2010, J Vis Exp.
Lamoyi et al., "Preparation of F(ab')2 Fragments from Mouse IgG of Various Subclasses," Methods in Enzymology, 1989, 121:652-663.
Lau et al., "Conjugation of Doxorubicin to Monoclonal Anti-carcinoembryonic Antigen Antibody via Novel Thiol-directed Cross-linking Reagents," Bioorg-Med-Chem., 1995, 3(10):1299-1304.
Lau et al., "Novel Doxorubicin-Monoclonal Anti-carcinoembryonic Antigen Antibody Immunoconjugate Activity in vitro," Bioorg-Med-Chem., 1995, 3(10):1305-12.
Lazar et al., "Engineered antibody Fc variants with enhanced effector function," Proc. Natl. Acad. Sci. USA, 2006, 103(11):4005-4010.
Lebowitz et al. "Modem analytical ultracentrifugation in protein science: A tutorial review," Protein Science, 2002, 11:2067-2079.
Lei et al., "Characterization of the Erwinia carotovora pelB gene and its product pectate lyase," J. Bacteriol., 1987, 169:4379.
Lemaire et al., "Insulin crystallization depends on zinc transporter ZnT8 expression, but is not required for normal glucose homeostasis in mice," Proc Natl Acad Sci USA, 2009, 106:14872-14877.
Lemaire et al., "Zinc transporters and their role in the pancreatic beta-cell," J Diabetes Investig, 2012, 3:202-211.
Lernmark et al., "Islet-cell-surface antibodies in juvenile diabetes mellitus," N Engl J Med, 978, 299:375-380.
Lippow et al., "Computational design of antibody-affinity improvement beyond in vivo maturation," Nat. Biotechnol., 2007, 25:1171-6.
Liston et al., "Beta-Cell Fragility As a Common Underlying Risk Factor in Type 1 and Type 2 Diabetes," Trends Mol Med, 2017, 23:181-194.

Lukowiak et al., "Identification and purification of functional human beta-cells by a new specific zinc-fluorescent probe," J Histochem Cytochem, 2001, 49:519-528.
Lund et al., "Human Fc gamma RI and Fc gamma RII interact with distinct but overlapping sites on human IgG," J Immun., Oct. 1991, 147:2657-62.
Mattila et al., "Extensive allelic sequence variation in the J region of the human immunoglobulin heavy chain gene locus," Eur. J. Immunol., 1995, 25:2578-2582.
Merriman et al., "A subclass of serum anti-ZnT8 antibodies directed to the surface of live pancreatic beta-cells," J Biol Chem, 2018, 293(2):579-587.
Merriman et al., "Down-regulation of the islet-specific zinc transporter-8 (ZnT8) protects human insulinoma cells against inflammatory stress," J Biol Chem, 2019, 294:16992-17006.
Merriman et al., "Highly specific monoclonal antibodies for allosteric inhibition and immunodetection of the human pancreatic zinc transporter ZnT8," J Biol Chem, 2018, 293:16206-16216.
Merriman et al., "Lipid-tuned Zinc Transport Activity of Human ZnT8 Protein Correlates with Risk for Type-2 Diabetes," J Biol Chem, 2016, 291:26950-26957.
Milenic et al, "Construction, Binding Properties, Metabolism, and Tumor Targeting of a Single-Chain Fv Derived from the Pancarcinoma Monoclonal Antibody CC49 ," Cancer Research, 1991, 51:6363-6371.
Millstein et al., "Hybrid hybridomas and their use in immunohistochemistry," Nature, Oct. 1983, 305:537-539.
Mizushima et al., "pEF-BOS, a powerful mammalian expression vector," Nucleic Acids Res., 1990, 18:5322.
Morgan et al., "The N-terminal end of the CH2 domain of chimeric human IgG1 anti-HLA-DR is necessary for C1q, Fc gamma RI and Fc gamma RIII binding," Immunology, 1995, 86(5):319-24.
Morton et al., "Kinetic analysis of macromolecular interactions using surface plasmon resonance biosensors," Methods in Enzymology, 1998, 295:268-294.
Mulligan et al., "Synthesis of rabbit β-globin in cultured monkey kidney cells following infection with a SV40 β-globin recombinant genome," Nature, 1979, 277:108-114.
Muratore et al., "The vascular architecture of the pancreatic islets: A homage to August Krogh," Comp Biochem Physiol A Mol Integr Physiol, 2021, 252:110846.
Neumann et al., "Gene transfer into mouse lyoma cells by electroporation in high electric fields," EMBO J. 1982, 1(7):841-845.
Neville et al, "Enhancement of Immunotoxin Efficacy by Acid-cleavable Cross-linking Agents Utilizing Diphtheria Toxin and Toxin Mutants," Journal of Biological Chemistry, 1989, 264(25):14653-14661.
Nicolson et al., "Insulin storage and glucose homeostasis in mice null for the granule zinc transporter ZnT8 and studies of the type 2 diabetes-associated variants," Diabetes, 2009, 58(9):2070-2083.
Noguchi et al., "Pharmacokinetic prediction of an antibody in mice based on an in vitro cell-based approach using target receptor-expressing cells," Sci Rep, 2020, 10:16268.
Ovacik et al., "Tutorial on Monoclonal Antibody Pharmacokinetics and Its Considerations in Early Development," Clin Transl Sci, 2018, 11:540-552.
Pantoliano et al, "Conformational stability, folding, and ligand-binding affinity of single-chain Fv immunoglobulin fragments expressed in *Escherichia coli*," Biochemistry, 1991, 30(42):10117-10125.
PCT International Preliminary Report on Patentability in International Application No. PCT/US2017/029250, dated Oct. 30, 2018, 5 pages.
PCT International Search and Written Opinion in International Application No. PCT/US2017/029250, dated Aug. 17, 2017, 6 pages.
Peterson et al., "A longlived IL-2 mutein that selectively activates and expands regulatory T cells as a therapy for autoimmune disease," J Autoimmun, 2018, 95:1-14.
Pierce et al., "Isothermal Titration Calorimetry of Protein-Protein Interactions," Methods, 1999, 19:213-221.
Pound et al., "Deletion of the mouse Slc30a8 gene encoding zinc transporter-8 results in impaired insulin secretion," Biochem J, 2009, 421:371-376.

(56) References Cited

OTHER PUBLICATIONS

Pound et al., "The physiological effects of deleting the mouse SLC30A8 gene encoding zinc transporter-8 are influenced by gender and genetic background," PLoS One, 2012, 7:e40972.
Rajpal et al., "A general method for greatly improving the affinity of antibodies by using combinatorial libraries," PNAS, 2005, 102(24):8466-71.
Roep et al., "Type 1 diabetes mellitus as a disease of the beta-cell (do not blame the immune system?)," Nat Rev Endocrinol, 2021, 17:150-161.
Rousseaux et al., "Optimal conditions for the preparation of proteolytic fragments from monoclonal IgG of different rat IgG subclasses," Methods in Enzymology, 1989, 121:663-669.
Saunders et al., "Ectonucleoside Triphosphate Diphosphohydrolase-3 Antibody Targets Adult Human Pancreatic beta Cells for In Vitro and In Vivo Analysis," Cell Metab, Mar. 2019, 29(3):745-754,e4.
Segerstolpe et al., "Single-Cell Transcriptome Profiling of Human Pancreatic Islets in Health and Type 2 Diabetes," Cell Metab, 2016, 24:593-607.
Shields et al, "High resolution mapping of the binding site on human IgG1 for Fc gamma RI, Fc gamma RII, Fc gamma RIII, and FcRn and design of IgG1 variants with improved binding to the Fc gamma R, High resolution mapping of the binding site on human IgG1 for Fc gamma RI, Fc gamma RII, Fc gamma RIII, and FcRn and design of IgG1 variants with improved binding to the Fc gamma R," J. Biol. Chem., 2001, 276(9):6591-604.
Shin et al., "Physical map of the 3' region of the human immunoglobulin heavy chain locus: clustering of autoantibody-related variable segments in one haplotype," EMBO J. 1991, 10:3641-3645.
Sjolander et al., "Integrated fluid handling system for biomolecular interaction analysis," Anal. Chem, 1991, 63:2338-2345.
Soja et al., "A chemical method for the deglycosylation of proteins," Arch. Biochem. Biophys., 1987, 259(1):52-57.
Stull et al., "Mouse islet of Langerhans isolation using a combination of purified collagenase and neutral protease," J Vis Exp., Sep. 2012, 67:4137.
Szabo et al., "Surface plasmon resonance and its use in biomolecular interaction analysis (BIA)," Curr. Opin. Struct. Biol. Oct. 1995, 5(5):699-705.
Takkinen et al., "An active single-chain antibody containing a cellulase linker domain is secreted by Escherichia coli," Protein Engineering, 1991, 4:837-841.
Tamura et al., "Structural Correlates of an Anticarcinoma Antibody: Identification of Specificity-Determining Residues (SDRs) and Development of a Minimally Immunogenic Antibody Variant by Retention of SDRs Only," Journal of Immunology, 2000, 164(3):1432-1441.
Thomas et al., "The natural autoantibody repertoire of nonobese diabetic mice is highly active," J Immunol, 2002, 169:6617-6624.
Thorpe et al., "New Coupling Agents for the Synthesis of Immunotoxins Containing a Hindered Disulfide Bond with Improved Stability in Vivo," Cancer Res., 1987, 47(22):5924-5931.
Thorpe et al., "The preparation and cytotoxic properties of antibody-toxin conjugates," Immunol. Rev., 1982, 62:119-58.
Thorp-Greenwood et al., "Multimodal radio—(PET/SPECT) and fluorescence imaging agents based on metallo-radioisotopes: current applications and prospects for development of new agents," Dalton Trans, 2011, 40(23):6129-6143.
Thotakura et al., "Enzymatic deglycosylation of glycoproteins," Meth. Enzymol., 1987, 138:350-359.
Tozzoli, "Receptor autoimmunity: diagnostic and therapeutic implications," Auto Immun Highlights, 2020, 11:1.
Urlaub et al., "Isolation of Chinese hamster cell mutants deficient in dihydrofolate reductase activity," Proc. Natl. Acad. Sci. USA, 1980, 77:4216-4220.
Vajdos et al., "Comprehensive functional maps of the antigen-binding site of an anti-ErbB2 antibody obtained with shotgun scanning mutagenesis," Journal of Molecular Biology, Jul. 2002, 320(2): 415-428.
Wan et al., "Proteoliposome-based full-length ZnT8 self-antigen for type 1 diabetes diagnosis on a plasmonic platform," Proc Natl Acad Sci USA, 2017, 114:10196-10201.
Ward et al., "Binding activities of a repertoire of single immunoglobulin variable domains secreted from Escherichia coli," Nature, Oct. 1989, 341:544-546.
Wigler et al., "Biochemical transfer of single-copy eucaryotic genes using total cellular DNA as donor," Cell, 1978, 14(3):725-731.
Wijesekara et al., "Beta cell-specific Znt8 deletion in mice causes marked defects in insulin processing, crystallisation and secretion," Diabetologia, 2010, 53:1656-1668.
Winkel et al., "Islet cell surface antibodies from insulin-dependent diabetics bind specifically to pancreatic B cells," J Clin Invest, 1982, 70:41-49.
Xue et al., "Cryo-EM structures of human ZnT8 in both outward- and inward-facing conformations," Elife, 2020, 9:e58823.
Akerfeldt et al., "Cytokine-induced beta-cell death is independent of endoplasmic reticulum stress signaling," Diabetes, 2008, 57(11):3034-3044.
Ashcroft et al., "Diabetes mellitus and the B cell: the last ten years," Cell, Mar. 16, 2012, 148(6):1160-71.
Atkinson et al., "How does type 1 diabetes develop?: the notion of homicide or beta-cell suicide revisited." Diabetes, 2011, 60(5):1370-1379.
Barlow et al., "Novel insights into pancreatic beta-cell glucolipotoxicity from real-lime functional analysis of mitochondrial energy metabolism in INS-1E insulinoma cells," Biochem J, 2013, 456(3):417-426.
Benton et al., "creening lambdagt recombinant clones by hybridization to single plaques in situ," Science, Apr. 1977, 196(4286):180-182.
Bodganov et al., "Lipids and topological rales governing membrane protein assembly," Biochim. Biophys. Acta, 2014, 1843(8):1475-1488.
Boesgaard et al., "The common SLC30A8 Arg325Trp variant is associated with reduced first-phase insulin release in 846 non-diabetic offspring of type 2 diabetes patients-the EUGENE2 study," Diabetologia, May 2008, 51(5):816-20.
Bonneford et al., "Rare and common genetic events in type 2 diabetes: what should biologists know?" Cell Metab, Mar. 2015, 21(3):357-68.
Brenner et al., "Encoded combinatorial chemistry," Proc. Natl. Acad. Sci. USA. Jun. 1992, 89(12):5381-5383.
Burbelo et al., "Luciferase Immunoprecipilalion Systems for Measuring Antibodies in Autoimmune and nfectious Diseases," Transl Res, 2015, 165:325-335.
Busch et al., "Increased fatty acid desaturation and enhanced expression of stearoyl coenzyme A desaturase protects Jancreatic beta-cells from lipoapoptosis," Diabetes, 2005, 54(10):2917-2924.
Butcher et al., "Association of proinflammatory cytokines and islet resident leucocytes with islet dysfunction in type 2 dliabetes," Diabetologia, 2014, 57(3):491-501.
Carell et al., "New promise in combinatorial chemistry: synthesis, characterization, and screening of small-molecule libraries in solution," Chem. Biol. 1995, 2(3):171-183.
Chabosseau et al., "Mitochondrial and ER-targeted eCALWY probes reveal high levels of free Zn2+," ACS Chem Biol, 2014, 9:2111-2120.
Chabosseau et al., "Zinc and diabetes, Arch Biochem Biophys," 2016, 611:79-85.
Chatterjee et al., "Type 2 diabetes," Lancet, Jun. 2017, 389(10085):2239-2251.
Cheng et al., "Prokaryotic Expression of Bioactive Zinc Transporter 8 Antigens and Detection of Diabetes Specific Autoantibodies in a Single Dot Immunogold Filtration Assay," Clin Lab, 2015, 10:1445-1452.
Cheng et al., "Tumor necrosis factor alpha-induced protein-3 protects zinc transporter 8 against proinflammatory cytokine-induced downregulation," Exp Ther Med, 2016, 12:1509-1514.
Cherezov et al., "Insights into the mode of action of a putative zinc transporter CzrB in Thermus thermophilus," Structure, Sep. 2008, 16(9):1378-88.

(56) References Cited

OTHER PUBLICATIONS

Chimienti et al., "Identification and cloning of a beta-cell-specific zinc transporter, ZnT-8, localized into insulin secretory granules," Diabetes, 2004, 53(9):2330-2337.

Chimienti et al., "In vivo expression and functional characterization of the zinc transporter Zn TB in glucose-induced nsulin secretion," J Cell Sci, Oct. 2006, 119(Pt 20):4199-4206.

Cnop et al., "Mechanisms of pancreatic beta-cell death in type 1 and type 2 diabetes: many differences, few imilarities," Diabetes, 2005, 54(Suppl 2):S97-107.

Cwirla et al., "Peptides on phage: a vast library of peptides for identifying ligands," Biochemistry 1990, 87(16):6378-6382.

Darmon et al., "Oriented reconstitution of red cell membrane proteins and assessment of their transmembrane disposition by immunoquenching of fluorescence," Biochimica et Biophysica Acta, 1985, 817:238-248.

Degorce et al., "HTRF: A technology tailored for drug discovery—a review of theoretical aspects and recent applications," Curr Chem Genomics, May 28, 2009, 3:22-32.

Delic-Sarac et al., "ELISA Test for Analyzing of Incidence of Type 1 Diabetes Autoantibodies (GAD and A2) in Children and Adolescents," Acta. Inform Med, 2016, 24:61-65.

Dudek et al., "Constitutive and inflammatory immunopeptidome of pancreatic beta-cells," Diabetes, 2012, 61(11):3018-3025.

Dunn, "Zinc-ligand interactions modulate assembly and stability of the insulin hexamer—a review," Biometals, Aug. 2005, 18(4):295-303.

Egefjord et al., "Zinc transporter gene expression is regulated by pro-inflammatory cytokines: a potential role for inc transporters in beta-cell apoptosis?" BMC Endocr Disord, 2009, 7(9).

Eide, "The oxidative stress of zinc deficiency," Metallomics, 2011, 3(11):1124-1129.

Eizirik et al., "The role of inflammation in insulitis and beta-cell loss in type 1 diabetes," Nat Rev Endocrinol, 2009, 5(4):219-226.

El Muayed et al., "Acute cytokine-mediated downregulation of the zinc transporter ZnT8 alters pancreatic beta-cell unction," J Endocrinol, 2010, 206 (2):159-169.

Enee et al., "ZnTB is a major COB+ T cell-recognized autoantigen in pediatric type 1 diabetes, Diabetes," 2012, 61(7):1779-1784.

Extended European Search Report in European Application No. 19849457.7, dated Jul. 13, 2022, 14 pages.

Fabregat et al., "The Reactome Pathway Knowledgebase," Nucleic Acids Res, 2018, 46(D1):D649-D655.

Farino et al., "Development, of a Rapid Insulin Assay by Homogenous Time-Resolved Fluorescence," PLoS One,2016, 11(2):e0148684.

Felder, "The Challenge of Preparing and Testing Combinatorial Compound Libraries in the Fast Lane, at the Front end of Drug Development,," Chimia 1994, 48:512-541.

Ferrannini et al., "Progression to diabetes in relatives of type 1 diabetic patients: mechanisms and mode of onset," Diabetes, 2010, 59(3):679-685.

Flannick et al., "Exome sequencing of 20,791 cases of type 2 diabetes and 24,440 controls," Nature, 2019, 570(7759):71-76.

Fonseca et ah, "Endoplasmic reticulum stress in beta-cells and development, of diabetes," Curr Opin Pharmacol, 2009, 9(6):763-770.

Foster et al., "Elemental composition of secretory granules in pancreatic islets of Langerhans," Biophys J, 1993, 64(2):525-532.

Fred et al., "Role of the AMP kinase in cytokine-induced human EndoC-belaH1 cell death, Mol Cell Endocrinol," 2015, 414:53-63.

Friend, et al., "Translational genomics. Clues from the resilien," Science, May 2014, 344(6187):970-2.

Gallop et al, "Applications of combinatorial technologies to drug discovery. 1. Background and peptide combinatorial libraries," J. Med. Chem., 1994, 37(9):1233-1251.

Gordon et al., "Applications of Combinatorial Technologies to Drug Discovery. 2. Combinatorial Organic Synthesis, Library Screening Strategies, and Future Directions," J Med. Chem. 1994, 37(10):1385-1401.

Grunstein et al., "Colony hybridization: a method for the isolation of cloned DNAs that contain a specific gene," Proc. Nat. Acad. Sci. USA, 1975, 72(10):3961-3965.

Gurgul-Convey et al., "Sensitivity profile of the human EndoC-betaH1 beta cell line to proinflammatory cytokines," Diabetologia, 2016, 59(10):2125-2133.

Hakonen et al., "MANF protects human pancreatic beta cells against, stress-induced cell death," Diabetologia, 2018, 61(10):2202-2214.

Hoch et al., "Histidine pairing at the metal transport site of mammalian ZnT transporters controls Zn2+ over Cd2+ selectivity," Proc Natl Acad Sci U S A, May 2012, 109(19):7202-7.

Homma et al., "SOD1 as a molecular switch for initiating the homeostatic ER stress response under zinc deficiency," Mol Cell, 2013, 52(1):75-86.

Hotamisligil et al., "Inflammation, metaflammation and immunometabolic disorders," Nature, 2017, 542(7640):177-185.

Houghten et al., "Generation and use of synthetic peptide combinatorial libraries for basic research and drug discovery," Nature, 1991, 354:84-86.

Houghten, "Peptide libraries: criteria and trends," Trends Genet, 1993, 9:235-239.

Huang, "Zinc and its transporters, pancreatic beta-cells, and insulin metabolism," Vitarn Horm, 2014, 95:365-390.

Ilonen et al., "Patterns of beta-cell autoantibody appearance and genetic associations during the first years of life," Diabetes, 2013, 32(10):3636-3640.

International Preliminary Report on Patentability in International Application No. PCT/US2020/036625, dated Dec. 7, 2021, 5 pages.

International Search Report and Written Opinion in International Application No. PCT/US2020/036625, dated Sep. 17, 2020, 7 pages.

Inzucchi et al., "Management of Hyperglycemia in type 2 diabetes: a patient-centered approach: position statement of the American Diabetes Association (ADA) and the European Association for the Study of Diabetes (EASD)," Diabetes Care, Jun. 2012, 35(6):1364-79.

Jaraosz-Chobot et al., "Rapid increase in the incidence of type 1 diabetes in Polish children from 1989 to 2004, and predictions for 2010 to 2025," Diabetologia, 2011, 54:508-515.

Jarchum et al., "In vivo cytotoxicity' of insulin-specific COB+ Tcells in HLA-A*0201 transgenic NOD mice," Diabetes, 2007, 56(10):2551-2560.

Kambe et al., "Current understanding of ZIP and ZnT zinc transporters in human health and diseases," Cell Mol Life Sci, 2014, 71:3281-3295.

Kay et al., "Overexpression of class I major histocompatibility complex accompanies insulitis in the nonobese diabetic mouse and is prevented by anti-interferon-gamma antibody," Diabetologia, 1991, 34(11):779-785.

Kharroubi et al., "Free fatty acids and cytokines induce pancreatic beta-cell apoptosis by different mechanisms: role of nuclear factor-kappaB and endoplasmic reticulum stress," Endocrinology, 2004, 145(11):5087-5096.

Kim et al., "Antibody Engineering for the Development of Therapeutic Antibodies," Molecules and Cells, 2005, 20(1):17-29.

Kimmel, "Identification and characterization of specific clones: strategy for confirming the validity of presumptive Iones," Methods in Enzymology, 1987, 152:507.

Klingensmith et al., "The presence of GAD and IA-2 antibodies in youth with a. type 2 diabetes phenotype: results from the TODAY study," Diabetes Care., 2010, 33:1970-1975.

Kodama et al., "Expression-Based Genome-Wide Association Study Links Vitamin D-Binding Protein With A\utoantigenicity in Type 1 Diabetes," Diabetes, 2016, 65(5):1341-1349.

Lam et al., "A new type of synthetic peptide library for identifying ligand-binding activity," Nature, 1991, 354:82-84.

Leahy et al., "Chronic hyperglycemia is associated with impaired glucose influence on insulin secretion. A study in normal rats using chronic in vivo glucose infusions," J Clin Invest, 1986, 77(3):908-915.

Lebl et al., "One-Bead-One-Structure Combinatorial Libraries," Biopolymers, 1995, 37:177-198.

(56) References Cited

OTHER PUBLICATIONS

Li et al., "A syntaxin 1, Galpha{o}, and N-type calcium channel complex at a presynaptic nerve terminal: analysis by quantitative immunocolocalization," J Neurosci, 2004, 24(16):4070-4081.

Li et al., "hZnT8 (S1c30a8) Transgenic Mice That Overexpress the R325W Polymorph Have Reduced Islet Zn2+ and Proinsulin Levels, Increased Glucose Tolerance After a High-Fat Diet, and Altered Levels of Pancreatic Zinc Binding Proteins," Diabetes, Feb. 2017, 66(2):551-559.

Li et al., "Identification of novel HLA-A 0201-restricled cytotoxic T lymphocyte epilopes from Zinc Transporter 8," Vaccine, 2013, 31(12):1610-1615.

Li et al., "Multiplexed Anli-Toxoplasma IgG, IgM and IgA Assay on Plasmonic Gold Chips: Towards Making Mass Screening Possible with Dye Test Precision," J Clin Microbiol, 2016, 54:1726-1733.

Li et al., "Temporal Proteomic Analysis of Pancreatic beta-Cells in Response to Lipotoxicity and Glucolipotoxicity," Mol Cell Proteomics, 2018, 17(11):2119-2131.

Lim et al., "High-efficiency screening of monoclonal antibodies for membrane protein crystallography," PLoS One, 2011, 6(9):e24653.

Liu et al., "Characterization of Zinc Influx Transporters (ZIPs) in Pancreatic beta Cells: Roles in Regulating Cytosolic Zinc Homeostasis and Insulin Secretion," J Biol Chem, 2015, 290(30):18757-18769.

Liu et al., "Proinsulin maturation, misfolding, and proteotoxicity," Proc Natl Acad Sci USA, 2007, 104:15841-15846.

Long et al., "Rising incidence of type 1 diabetes is associated with altered immunophenotype at diagnosis," Diabetes, 2012, 61:683-686.

Lu et al., "Structural basis for autoregulalion of the zinc transporter YiiP," Nat Struct. Mol Biol, 2009, 16:1063-1067.

Madden et al., "Synthetic Combinatorial Libraries: Views on Techniques and Their Application,," Perspectives in Drag Discovery and Design, 1995, 2:269-282.

Maedler et al., "Distinct effects of saturated and monounsaturated fatty acids on betacell turnover and function," Diabetes, 2001, 50(1):69-76.

Meng et al., "Epoxomicin, a potent and selective proteasome inhibitor, exhibits in vivo antiinflammatory activity," Proc Natl Acad Sci USA, 1999, 96(18):10403-10408.

Mittermayer et al., "Addressing unmet medical needs in type 2 diabetes: a narrative review of drugs under :levelopmenl," Curr Diabetes Rev, 2015, 11(1):17-31.

Murata et al., "The immunoproteasome and thymoproteasome: functions, evolution and human disease," Nat Immunol, 2018, 19(9):923-931.

NCBI Accession No. ABQ59023. 1, "SLC30A8 protein [*Homo sapiens*]".

NCBI Accession No. KR712225. 1, "Synthetic construct *Homo sapiens* clone CCSBHm 00900180 SLC30A8 (SLC30A8) mRNA, encodes complete protein."

Ohana et al., "Identification of the Zn2+ binding site and mode of operation of a mammalian Zn2+ transporter," J Biol Chem, Jun. 2009, 284(26):17677-86.

Ohashi et al., "Zinc Transporter SLC39A7/ZIP7 Promotes Intestinal Epithelial Self-Renewal by Resolving ER Stress," DLoS Genet, 2016, 12 (10):e1006349.

Parsons et al., "The C-terminal cytosolic domain of the human zinc transporter ZnT8 and its diabetes risk variant," FEBS J, 2018, 285(7):1237-1250.

PCT International Preliminary Report on Patentability in International Application No. PCT/US2019/046747, dated Feb. 16, 2021, 7 pages.

PCT International Search Report and Written Opinion in International Application No. PCT/US2019/046747, dated Nov. 28, 2019, 8 pages.

PCT Invitation to Pay Additional Fees And, Where Applicable, Protest Fee in International Application No. PCT/US2022/075156, dated Nov. 3, 2022, 2 pages.

Pearson, "Zinc transport and diabetes risk," Nat Genet, Apr. 2014, 46(4):323-4.

Pettersen et al., "UCSF Chimera—a visualization system for exploratory research and analysis," J Comput Chem, Oct. 2004, 25(13):1605-12.

Pietropaolo et al., "Primer: immunity and autoimmunity," Diabetes, 2008, 57(11):2872-2882.

Pluckthun et al., "Expression of functional antibody Fv and Fab fragments in *Escherichia coli*," Methods in Enzymology, 1989, 178:497-515.

Poitout et al., "Glucolipotoxicity of the pancreatic beta cell," Biochim Biophys Acta, 2010, 1801(3):289-298.

Prasad et al., "Genetics of Type 2 Diabetes—Pitfalls and Possibilities," Genes (Basel), Mar. 2015, 6(1):87-123.

Punjani et al., "cryoSPARC: algorithms for rapid unsupervised cryo-EM structure determination," Nat Methods, Mar. 2017, 14(3):290-296.

Qian et al., "Screening and identification of human ZnT8-specific single-chain variable fragment (scFv) from type 1 diabetes phage display library," Science China Life Sciences, Jun. 2016, 59(7):686-693.

Ravassard et al., "A genetically engineered human pancreatic beta cell line exhibiting glucose-inducible insulin secretion," J Clin Invest, 2011, 121(9):3589-3597.

Regazzi et al., "VAMP-2 and cellubrevin are expressed in pancreatic beta-cells and are essential for Ca(2+)-but not or GTP gamma S-induced insulin secretion," EMBO J, 1995, 14(12)2723-2730.

Robertson et al., "Beta-cell glucose toxicity, lipotoxicity, and chronic oxidative stress in type 2 diabetes," Diabetes, 2004, 53(Suppl 1):S119-124.

Rohou et al., "CTFFIND4: Fast, and accurate defocus estimation from electron micrographs," J Struct Biol, Nov. 2015, 192(2)216-21.

Rojas et al., "Pancreatic Beta Cell Death: Novel Potential Mechanisms in Diabetes Therapy," J Diabetes Res, 2018, 9601801.

Rutter, "Think zinc: New roles for zinc in the control of insulin secretion," Islets, Jan.-Feb. 2010, 2(1):49-50.

Saltiel et al., "Inflammatory mechanisms linking obesity and metabolic disease," J Clin Invest, 2017, 127(1):1-4.

Scheres, "RELION: implementation of a Bayesian approach to cryo-EM structure determination," J Struct Biol, Dec. 2012, 180(3):519-30.

Scheuner et al., "The unfolded protein response: a pathway that links insulin demand with beta-cell failure and diabetes," Endocr Rev, 2008, 29(3):317-333.

Schuit et al., "Glucose stimulates proinsulin biosynthesis by a dose-dependent recruitment, of pancreatic beta cells," Droc Natl Acad Sci USA, 1988, 85(11):3865-386.

Schwanhausser et al., "Global quantification of mammalian gene expression control," Nature, 2011, 473:337-342.

Scott et al., "A genome-wide association study of type 2 diabetes in Finns detects multiple susceptibility variants," Science, Jun. 2007, 316(5829):1341-5.

Scotto et al., "Zinc transporter {ZnT}8{186-194) is an immunodominant COB+ T cell epitope in HLA-A2+ type 1 dliabetic patients," Diabetologia, 2012, 55(7):2026-2031.

Skarstrand et al., "Zinc transporter 8 (ZnT8) autoantibody epitope specificity and affinity examined with ecombinant ZnT8 variant, proteins in specific ZnT8R and ZnT8W autoantibody-positive type 1 diabetes patients," Clinical & Experimental Immunology, 2015, 179(2):220-229.

Solimena et al., "ICA 512, an autoantigen of type I diabetes, is an intrinsic membrane protein of neurosecretory granules," EMBO J, 1996, 15(9):2102-2114.

Sosenko et al., "The Use of Electrochemiluminescence Assays to Predict Autoantibody and Glycemic Progression Toward Type 1 Diabetes in Individuals with Single Autoantibodies," Diabetes Technol Ther, 2017, 3:183-187.

Steck et al., "Predictors of Progression From the Appearance of Islet Autoantibodies to Early Childhood Diabetes: The Environmental Determinants of Diabetes in the Young (TEDDY)," Diabetes Care., 2015, 38(5):808-813.

(56) References Cited

OTHER PUBLICATIONS

Stumvoll et al., "Type 2 diabetes: principles of pathogenesis and therapy," Lancet, Apr. 9-15, 2005, 365(9467):1333-46.
Sun et al., "Gene silencing of ZnT8 attenuates inflammation and protects pancreatic tissue injury in T1D," Immunology Letters, Jun. 2018, 198:1-6.
Surface Plasmons on Smooth and Rough Surfaces and on Gratings, Springer Verlag, 1988, 140 pages.
Szoka et al., "Comparative properties and methods of preparation of lipid vesicles (liposomes)," Annu Rev Biophys Bioeng, 1980, 9:467-508 9.
Tabakman et al., "Plasmonic substrates for multiplexed protein microarrays with femlomolar sensitivity and broad dynamic range," Nat Commun.
Tamaki et al., "The diabetes-susceptible gene SLC30A8/ZnT8 regulates hepatic insulin clearance," J Clin Invest, Oct. 2013, 123(10):4513-24.
Taylor et al., "Protein kinase CK2 triggers cytosolic zinc signaling pathways by phosphorylation of zinc channel ZIP7," Sci Signal, 2012, 5(210):ra11.
Thul et al., "A subcellular map of the human proteome," Science, 2017, 356(6340):eaa13321.
Tiberti et al., "Detection of four diabetes specific autoantibodies in a single radioimmunoassay: an nnovative high-throughput approach for autoimmune diabetes screening," 2011, Clin Exp Immunol 3:317-324.
Tsai et al., "Are obesity-related insulin resistance and type 2 diabetes autoimmune diseases?" Diabetes, 2015, 64(6):1886-1897.
Tuncay et al., "Hyperglycemia-Induced Changes in ZIP7 and ZnT7 Expression Cause Zn{2+) Release From the Sarco(endo)plasmic Reticulum and Mediate ER Stress in the Heart," Diabetes, 2017,66(5):1346-1358.
Ustinova et al., "Characterization of monoclonal ZnT8-specific antibody," Frontiers in Immunology, Jan. 2013, retrieved from URL<https://internal-www.frontiersin.org/Community/AbstractDetails.aspx?ABS_DOI=10.3389/conf.fimmu.2013.02.00326&eid=&sname=>, 2 pages.
Vinkenborg et al., "Genetically encoded FRET sensors to monitor intracellular Zn2+ homeostasis," Nat Methods, 2009, 6(10):737-740.
Vyas et al., "Molecular recognition of oligosaccharide epitopes by a monoclonal Fab specific for Shigella flexneri Y ipopolysaccharide: X-ray structures and thermodynamics," Biochemistry, Nov. 19, 2002, 41(46):13575-86.
Wahl, "Molecular hybridization of immobilized nucleic acids: theoretical concepts and practical considerations," Methods in Enzymology, 1987, 152:399.
Wenzlau et al.. "A common nonsynonymous sinde nucleotide polymorphism in the SLC30A8 gene determines ZnT8 Autoantibody specificity in type 1 diabetes," Diabetes, 2008, 57(10):2693-2697.
Wenzlau et al., "Changes in Zinc Transporter 8 Autoantibodies Following Type 1 Diabetes Onset: The Type 1 Diabetes Genetics Consortium Autoantibody Workshop," Diabetes Care, 2015, 38(Supplement 2):S14-20.
Wenzlau et al., "Novel diabetes autoantibodies and prediction of type 1 diabetes," Current Diabetes Reports, 2013, 13:608-615.
Wong et al., "Exploring the Association Between Demographics, SLC30A8 Genotype, and Human Islet Content of Zinc, Cadmium, Copper, Iron, Manganese and Nickel," Sci Rep, 2017, 7(1):473.

Woodruff et al., "The Zinc Transporter SLC39A7 (ZIP7) Is Essential for Regulation of Cytosolic Zinc Levels," Mol Pharmacol, 2018, 94(3):1092-1100.
Wu et al., "An electrochemiluminescence (ECL)-based assay for the specific detection of anti-drug antibodies of the IgE isotvpe," J Pham Biomed Anal, 2013, 86:73-81.
Yu et al., "Antiislet autoantibodies usually develop sequentially rather than simultaneously," Journal of Clinical Endocrinology & Metabolism, 1996, 81(12):4264-4267.
Yu et al., "Early expression of antiinsulin autoantibodies of humans and the NOD mouse: evidence for early dietermination of subsequent diabetes," Proc Nall Acad Sci USA, 2000, 97(4):1701-1706.
Yu et al., "Identification of Candidate Tolerogenic CD8(+) T Cell Epitopes for Therapy of Type 1 Diabetes in the NOD Mouse Model," J Diabetes Res, 2016, 2016:9083103.
Yu et al., "Proinsulin/Insulin autoantibodies measured with electrochemiluminescent assay are the earliest indicator of prediabetic islet autoimmunity." Diabetes Care, 2013, 36(8):2266-2270.
Zeggini et al., "Replication of genome-wide association signals in UK samples reveals risk loci for type 2 diabetes," Science, Jun. 1, 2007, 316(5829):1336-41.
Zhang et al., "A plasmonic chip for biomarker discovery and diagnosis of type 1 diabetes," Nat Med, 2013, 20:948-953.
Zhang et al., "A Simple Statistical Parameter for Use in Evaluation and Validation of High Throughput Screening Assays," J Biomol Screen, 1999, 4(2):67-73.
Zhang et al., "Diagnosis of Zika virus infection on a nanotechnology platform," Nat Med 2017, 23:548-550.
Ziegler et al., "Seroconversion to multiple islet autoantibodies and risk of progression to diabetes in children," JAMA, 2013, 309(23):2473-2479.
Zumsteg et al., "Nitric oxide production and Fas surface expression mediate two independent pathways of cytokinenduced murine beta-cell damage," Diabetes, 2000, 49(1):39-47.
Extended European Search Report in European Application No. 18832105.3, dated Mar. 11, 2021, 11 pages.
GenBank Accession No. NM_001172814.1, "*Homo sapiens* solute carrier family 30 (zinc transporter), member 8 (SLC30A8), transcript variant 2, mRNA," dated Mar. 15, 2015, 5 pages.
Hwang et al., "Budding yeast Cdc20: a target of the spindle checkpoint," Science, Feb. 1998, 279(5353):1041-1044 (abstract only).
International Preliminary Report on Patentability in International Appln. No. PCT/US2018/040890, dated Jan. 14, 2020, 6 pages.
International Search Report and Written Opinion in International Appln. No. PCT/US2018/040890, dated Oct. 25, 2018, 8 pages.
International Search Report and Written Opinion in International Appln. No. PCT/US2022/075156, dated Jan. 10, 2023, 13 pages.
Koh et al., "Visible to Near-Infrared Fluorescence Enhanced Cellular Imaging on Plasmonic Gold Chips," small, Jan. 27, 2016, 12(4):457-465 (abstract only).
European Search Report in European Application No. 20817829.3, dated Jun. 1, 2023, 20 pages.
Gu et al., "Identification of Autoantibodies to ZnT8 Extracellular Epitope(s) in Patients with T1D," Diabetes, 79th Scientific Sessions of the American-Diabetes-Association (ADA), Jun. 7-11, 2019, 68(Suppl. 1):162-OR.

* cited by examiner

ZNT8 ASSAYS FOR DRUG DEVELOPMENT AND PHARMACEUTICAL COMPOSITIONS

REFERENCE TO RELATED APPLICATIONS

This application is a continuation of U.S. patent application Ser. No. 16/095,394, filed Oct. 22, 2018, which is a 35 U.S.C. § 371 U.S. national entry of International Application PCT/US2017/029250, having an international filing date of Apr. 25, 2017, which claims the benefit of U.S. Provisional Application No. 62/326,871, filed Apr. 25, 2016, the content of each of the aforementioned applications is herein incorporated by reference in their entirety.

STATEMENT OF GOVERNMENTAL INTEREST

This invention was made with government support under grant no. R01 GM065137-13 from the National Institutes of Health. The government has certain rights in the invention.

BACKGROUND OF THE INVENTION

The escalating type-2 diabetes (T2D) epidemic is a major global health concern. Given that T2D is partly genetically determined, genetic factors that increase T2D susceptibility enhance related medical complications and lower the life spans of patients with T2D. Recent advances in genome-wide association studies (GWASs) revived the initial optimism of identifying T2D susceptibility genes and accelerated the discovery of these susceptibility gene for diabetes. Genes affecting risk for T2D have been published including the zinc transporter, member 8 (SLC30A8) gene also known at ZnT8. ZnT8 is one or nine human genes of multi-spanning transmembrane proteins facilitating $Zn^{2+}$ efflux from the cell and sequestration into intracellular compartments. Within the pancreas, specifically in the islet, there are specific zinc transporter (ZnT8) that mediates zinc enrichment in insulin secretory granules of pancreatic beta cells. There are known variants of ZnT8 DNA and protein sequences including a nonsynonymous variant of human ZnT8 (R325W) that is thought to contribute to the susceptibility of type-2 diabetes (T2D), but it remains unclear how the risk allele correlates with zinc transport.

SUMMARY OF THE INVENTION

This application includes a method of identifying a drug to treat or prevent diabetes in subjects comprising the steps of: providing a proteoliposome with a zinc transporter ZnT8, or functional part thereof; administering an agent to the proteoliposome forming a treated sample; measuring the activity of the zinc transporter ZnT8 in the treated sample to obtain a first activity measurement and comparing the first activity measurement to a second activity measurement of a reference; and identifying the drug when the first activity measurement is lower than the second activity measurement. The preferred reference are proteoliposome with a ZnT8 transporter or variant thereof substantially free of agent. A suitable activity of zinc transporter ZnT8 measured in the present invention is the rate of zinc transport efficiency wherein the first measurement is from 1.3, 1.4, 1.5, 1.6, 2.0, 2.2, 2.4, 2.8, 3.0, 3.2, 3.4, 3.6, 3.8, 4.0, 4.2, 4.4, 4.6 to 5.0, 5.2, 5.4, 5.6, 5.8, 6.0, 6.2, 6.4, 6.6, 6.8, 7.0, 7.2, 7.4, 7.6, 7.8, 8.0, 9.0, 10.0, 11.0, 15.0 fold lower than the second measurement and wherein the rate of zinc transport efficiency is based on a Vmax/Km value using stopped-flow kinetics.

Another embodiment of the present invention is a method of identifying a drug to treat or prevent diabetes in subjects comprising the steps of: providing a first sample that expresses a zinc transporter ZnT8, or functional part thereof administering an agent to the first sample forming a treated sample; measuring the activity of the zinc transporter ZnT8 in the treated sample to obtain a first activity measurement and comparing the first activity measurement to a second activity measurement of a reference; and identifying the drug when the first activity measurement is lower than the second activity measurement. Suitable zinc transporters used in the present invention include the nonsynonymous variant of human ZnT8 (R325W) and a ZnT8 protein or peptide that has activity and is modified such as with a tag, such as a His-tag. The sample may be in vitro human cells such as HEK293 cells that stably express ZnT8 or a biological sample obtained from a subject such as a biopsy, cells, or tissue. There are alternative ways in which the activity of the zinc transporter ZnT8 is measured including measuring the intracellular zinc accumulation in the sample or the rate of zinc transport efficacy wherein the first activity measurement is from 1.3, 1.4, 1.5, 1.6, 2.0, 2.2, 2.4, 2.8, 3.0, 3.2, 3.4, 3.6, 3.8, 4.0, 4.2, 4.4, 4.6 to 5.0, 5.2, 5.4, 5.6, 5.8, 6.0, 6.2, 6.4, 6.6, 6.8, 7.0, 7.2, 7.4, 7.6, 7.8, 8.0, 9.0, 10.0, 11.0, 15.0 fold lower than the second activity measurement. Typically, the rate of zinc transport efficiency is based on a Vmax/Km value using stopped-flow kinetics. The agent is selected from the group comprising an antibody, portion of an antibody, nucleic acid, peptide, protein, chemical or combination thereof.

Another embodiment of the present invention is a pharmaceutical composition comprising a drug of the present invention, salt, solvate, or stereoisomer thereof. The present invention identified lipids that inhibit the activity of ZnT8, specifically lysophosphatidylcholines, cholesterols, or combinations thereof and example of a drug of the present invention.

Another embodiment of the present invention is a method of inhibiting ZnT8 activity in pancreas cells of a subject comprising administering to the subject an effective amount of the drug of the present invention, salt, solvate, or stereoisomer thereof An additional step to this method may be having the ZnT8 activity measured in a sample taken from the subject before and after the subject is administered the drug by determining the rate of zinc transport efficiency in the sample. The rate of zinc transport efficiency after the subject is administered the drug is from 1.3, 1.4, 1.5, 1.6, 2.0, 2.2, 2.4, 2.8, 3.0, 3.2, 3.4, 3.6, 3.8, 4.0, 4.2, 4.4, 4.6 to 5.0, 5.2, 5.4, 5.6, 5.8, 6.0, 6.2, 6.4, 6.6, 6.8, 7.0, 7.2, 7.4, 7.6, 7.8, 8.0, 9.0, 10.0, 11.0, 15.0 fold lower than before the subject was administered the drug. The rate of zinc transport efficiency is preferably based on a Vmax/Km value using stopped-flow kinetics.

Another embodiment of the present invention is a method of treating or preventing diabetes in a subject comprising administering to the subject an effective amount of the drug of the present invention, salt, solvate, or stereoisomer thereof.

Another embodiment of the present invention is a method of purifying a zinc transporter ZnT8 comprising the steps of: providing a crude preparation of a zinc transporter ZnT8 comprising proteins other than the zinc transporter ZnT8; reconstituting the crude preparation of the zinc transporter ZnT8 in a liposome forming a transporter proteoliposome comprising the ZnT8 in a solution; separating the solution from the transporter proteoliposone; and forming a purified zinc transporter ZnT8. Suitable liposomes used in the present invention comprise a lipid including anionic phospholipids, non-bilayer phospholipids, cholesterol, phosphatidylinositol (PI), phosphatidylserine (PS), lysophosphatidylcholine (LPC), cholesterol, or a combination thereof. The crude preparation of zinc transporter ZnT8 is reconstituted in a liposome to maintain the activity of zinc transporter ZnT8 during the separation step, such as centrifugation, for example. The method of the present invention not only creates a highly purified zinc transporter ZnT8, but a purified Zinc transporter ZnT8 having a Vmax greater than 4, greater than 5, or greater than 6. The purified zinc transporter ZnT8 of the present invention may be in the R-conformation, the W-conformation, or a combination thereof. A crude preparation of zinc transporter ZnT8 used in the present invention may be defined as a product of affinity purification, typically where the affinity purification comprises metal affinity resins, for example. The methods of the present invention may include additional steps such as detecting anti-ZnT8 autoantibodies in a subject using the purified zinc transporter ZnT8, thereby diagnosing type-1 diabetes in a subject. The method of the present invention may generate anti-ZnT8 mAbs such as humanized anti-ZnT8 mAbs that are conformational specific, for example. Other steps include performing diagnostic beta-cell imaging using the antibodies of the present invention or creating a mAb-based therapeutic ZnT8 inhibitors using the antibodies of the present invention.

The term "activity" refers to the ability of a gene to perform its function such as ZnT8 (a zinc transporter) being able to transport zinc.

The term "express" refers to the ability of a gene to express the gene product including for example its corresponding mRNA or protein sequence (s).

The term "reference" refers to a standard or control conditions such as a sample (human cells) or preoteolipisomes with a zinc transporter ZnT8 free, or substantially free, of agent.

The term "subject" refers to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The term "ZnT8" is intended to refer to the (SLC30A8) gene and variants as well as products including nucleic acid and protein sequences derived therefrom. ZnT8 includes modified nucleic acid and amino acid sequences including tags for visualization for example. Examples of ZnT8 nucleic acid and protein sequences suitable for the present invention include: *Homo sapiens* clone SLC30A8 DNA sequence having a NCBI Accession Number KR712225.1 and *Homo sapiens* SLC30A8 protein sequence having a NCBI Accession Number ABQ59023.1 as examples. An example of a ZnT8 gene sequence is SLC30A8 solute carrier family 30 member 8 [*Homo sapiens* (human)] having an NCBI Gene ID: 169026. The ZnT8 used in the present invention may be eukaryotic including human and animal or prokaryotic including bacterial ZnT8 transporters.

BRIEF DESCRIPTION OF THE DRAWINGS

FIG. 1A illustrates Western blotting analysis of inducible expression of ZnT8 variants. FIG. 1B illustrates intracellular localization of ZnT8 expression by immunofluorescence. FIG. 1C illustrates imaging of intracellular zinc accumulation. FIG. 1D illustrates the time course of zinc accumulation.

FIG. 2A illustrates a homology model of human ZnT8. FIG. 2B illustrates the purification and reconstitution of ZnT8 variants. FIG. 2C illustrates the sizing of HPLC profiles of the purified ZnT8.

FIG. 3A illustrates the fluorescence responses to increasing zinc concentrations. FIG. 3B illustrates the steady state kinetics.

DETAILED DESCRIPTION OF THE INVENTION

Figure 1A:
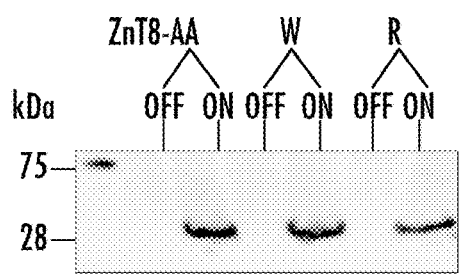
FIG. 1A-1D illustrates the induced expression and characterization of human ZnT8 variants.

The islet-specific zinc transporter ZnT8 mediates zinc enrichment in insulin secretory granules of pancreatic beta cells. A nonsynonymous variant of human ZnT8 (R325W) contributes to the susceptibility of type-2 diabetes (T2D), but it remains unclear how the risk allele correlates with zinc transport. Here we report a comparative analysis of a pair of high-risk (R325) and low-risk (W325) variant. The R-form was found hyperactive following induced expression in HEK293 cells. Reconstitution of purified R-form into biomimetic membranes yielded a 51% increase in the transport rate. During insulin granule biogenesis, the hosting membrane of ZnT8 undergoes enormous lipid remodeling. ZnT8 variants were shown functionally tunable to stimulation by anionic phospholipids and inhibition by cholesterol and non-bilayer phospholipids. Over a broad range of permissive lipid compositions, the R-form consistently exhibited accelerated zinc transport kinetics, indicating that the high-risk variant may be targeted for inhibition to reduce T2D risk in the general population.

Zinc forms stable complexes with insulin hexamers, enabling crystalline packing of the secretory granules of pancreatic beta cells. Defective insulin secretion in the face of insulin resistance is a main physiological characteristic of T2D, a complex multifactorial polygenetic disease with more than 80 T2D-susceptibility loci/genes identified so far by genome-wide association studies (GWASs). A nonsynonymous single nucleotide polymorphism in SLC30A8 (rs13266634 C>T), which causes an arginine to tryptophan change at position 325 (R325W), is associated with a 53% increased risk of developing T2D (Sladek R, Rocheleau G, Rung J, Dina C, Shen L, Serre D, Boutin P, Vincent D, Belisle A, Hadjadj S, et al. (2007) *Nature*. 445, 881-885). The risk allele is widespread in more than 50% of the population according to HapMap data (build 35). SLC30A8 encodes a granular zinc transporter known as ZnT8. In pancreatic beta cells, ZnT8 is highly expressed and responsible for transporting cytosolic zinc into insulin granules. However, the molecular mechanism underlying the genetic susceptibility of ZnT8 polymorphisms remains controversial. ZnT8 inactivation in various mouse models revealed large phenotypic variations ranging from decreased, unchanged to even enhanced insulin secretion. Over-expression and functional characterization of polymorphic alleles in pancreatic beta cells suggested an attenuated zinc transport activity associated with an increased T2D susceptibility, whereas genotyping rare nonsense and frameshift mutations of ZnT8 in humans indicated an opposite causal relationship, suggesting that a loss of function of ZnT8 actually reduced T2D risk. The conflicting results concerning the directional relationship between ZnT8 activity and T2D susceptibility prevent the identification of specific defects in the risk variant for pharmacological correcting. At present, it is not clear whether stimulation or inhibition of ZnT8 might be a therapeutic option to reduce T2D risk in the general population.

Studies of the functional effects of GWAS-identified risk variants in humans are challenged by small effect sizes that in general do not provide a clinically useful predictor for disease risk. Although protective effects on T2D risk were observed in loss-of-function ZnT8 mutants at an occurrence rate of about 350 carriers out of 150,000 genotyped individuals, the extrapolation of the casual relationship obtained from rare penetrant mutants to common, yet mild ZnT8 polymorphic variants is not straightforward, because in humans the relationship between ZnT8 activity and diabetes risk could follow a complex bell-shaped dose-response. To determine the functional effects of the common ZnT8 polymorphic variants on T2D risk, we developed induced expression of human ZnT8 variants in HEK293 cells, purified both the R- and W-form in a native state, and achieved reconstitution in biomimetic membranes with defined lipid compositions. A direct functional comparison of human ZnT8 polymorphic variants at the molecular level sidestepped inherent limitations to phenotypic interpretation of animal models. Our experiments demonstrated a clear causality between elevated zinc transport activity and increased T2D risk.

Induced Expression and Characterization of Human ZnT8 Variants.

Figure 1B:
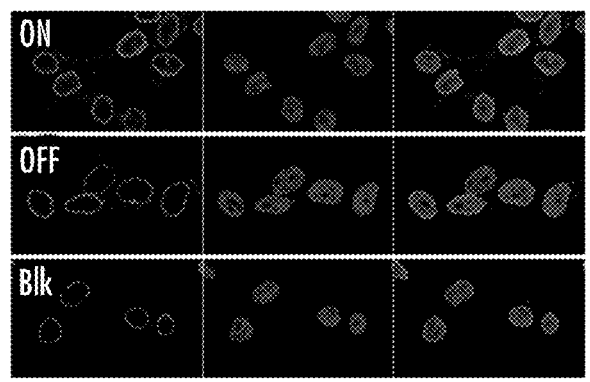
Figure 1C:
Figure 1D:
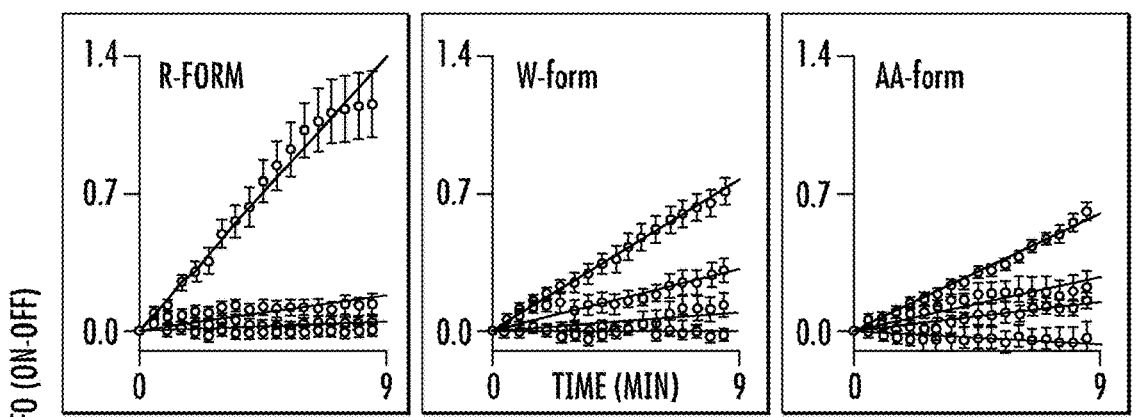
Figure 1D:
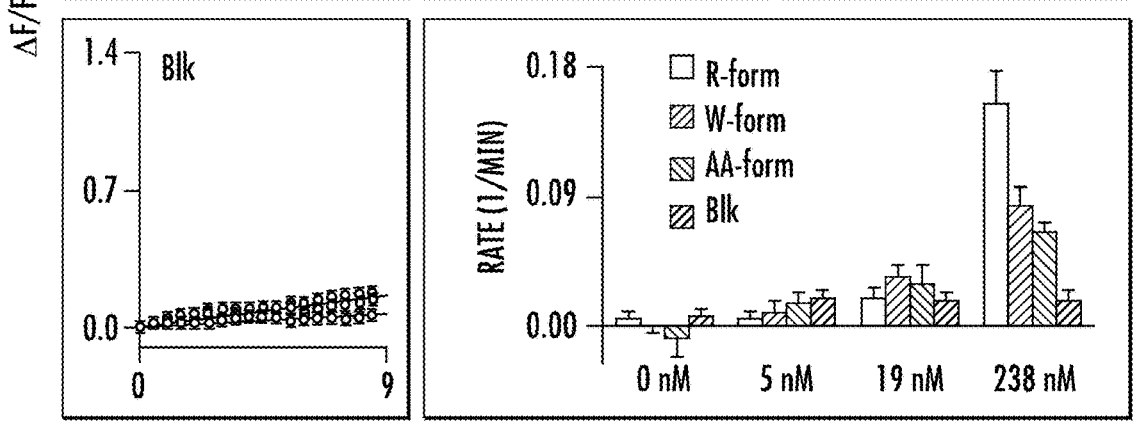

In human pancreatic islets, ZnT8 expression is confined intracellularly to the beta cells and alpha cells to a lesser extent. To produce recombinant human ZnT8 variants, we generated a series of stable HEK293 cell lines, each with an isogenic integration of a His-tagged ZnT8 variant under a tetracycline-inducible promoter. Western blotting using an antibody to the His-tag showed that the induced R- or W-form reached a similar level of expression while the uninduced basal level was suppressed below the detection limit (FIG. 1A). A two-fold increase of post-induction expression level was observed for a ZnT8 mutant (termed the AA-form) containing a double Ala-substitution to the predicted transport-site. ZnT8 variants were also monitored for induced expression in HEK293 cells by immunofluorescence labeling and confocal microscopy. Post-induction immunoreactivities toward the His-tag were found predominantly restricted to the cytoplasm (FIG. 1B). Additional strong immunostaining of the nuclear envelope was observed due to non-specific antibody binding as shown by the same staining pattern in uninduced cells and in HEK293 cells with no genomic ZnT8 integration as a negative control. This cell line is referred to hereafter as blank (Blk). The effects of ZnT8 over-expression on intracellular labile zinc concentrations were examined using a membrane-permeable zinc-selective fluorescent indicator, Zinpyr-1. Zinpyr-1 labeling produced bright punctate staining in the juxtanuclear region (FIG. 1C), consistent with the trapping of Zinpyr-1 in the Golgi and acidic subcellular compartments. Cells with induced expression of the R-form exhibited stronger Zinpyr-1 staining than the W- and AA-form. The basal level of Zinpyr-1 fluorescence in Blk was significant, at a level similar to that of the W- and AA-form (FIG. 1C). Quantification of Zinpyr-1 fluorescence in ~13,000 live cells by flow cytometry yielded a mean fluorescence intensity of 2860.3±9.6 for the R-form and 2135.4±7.6 for the W-form, respectively. This result supported a higher level of vesicular zinc accumulation by induced expression of the R-form. We next monitored ZnT8-mediated vesicular zinc accumulation in real time. Stable expression cells or Blk in a 96-well microplate were loaded with Zinpyr-1, and then exposed to a zinc uptake buffer containing 1 uM pyrithione, a zinc ionophore that was used to break down the surface membrane barrier to zinc diffusion, enabling direct manipulation of the cytosolic free zinc concentration. Zinc exposure at 15° C. triggered a linear rise of Zinpyr-1 fluorescence within 10 min, which could be quenched by a zinc chelator TPEN. The net fluorescence difference between induced and uninduced cells reflected ZnT8-mediated vesicular zinc accumulation (FIG. 1D). The rate of zinc uptake increased progressively with an increasing free zinc concentration from 5 nM to 383 nM. At lower zinc concentrations (5 and 19 nM), the rate of three ZnT8 variants showed no significant difference at a level similar to that of Blk. However, at 383 nM, the R-form exhibited a significantly faster rate of zinc accumulation than the W-form, indicating that the R-form was hyperactive with respect to the W-form. The rates of the W- and AA-form were significantly faster than the basal level of Blk, suggesting that both variants were active. At 383 nM, the rank order of zinc transport activity was R>W>AA>Blk following induced expression in HEK293 cells (FIG. 1D).

Purification and Reconstitution of ZnT8 Variants.

Figure 2A:
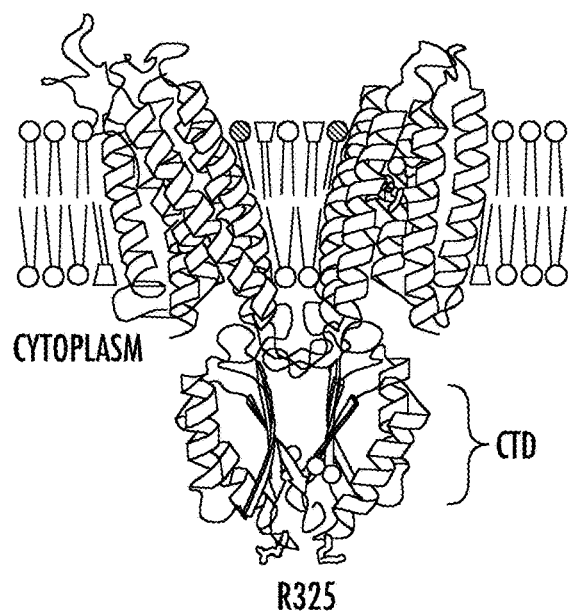
FIG. 2A-2C illustrates the purification of human ZnT8 variants.
Figure 2B:
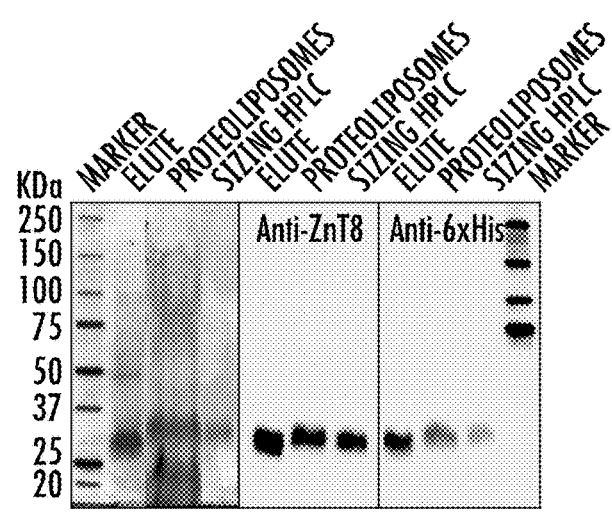
Figure 5:
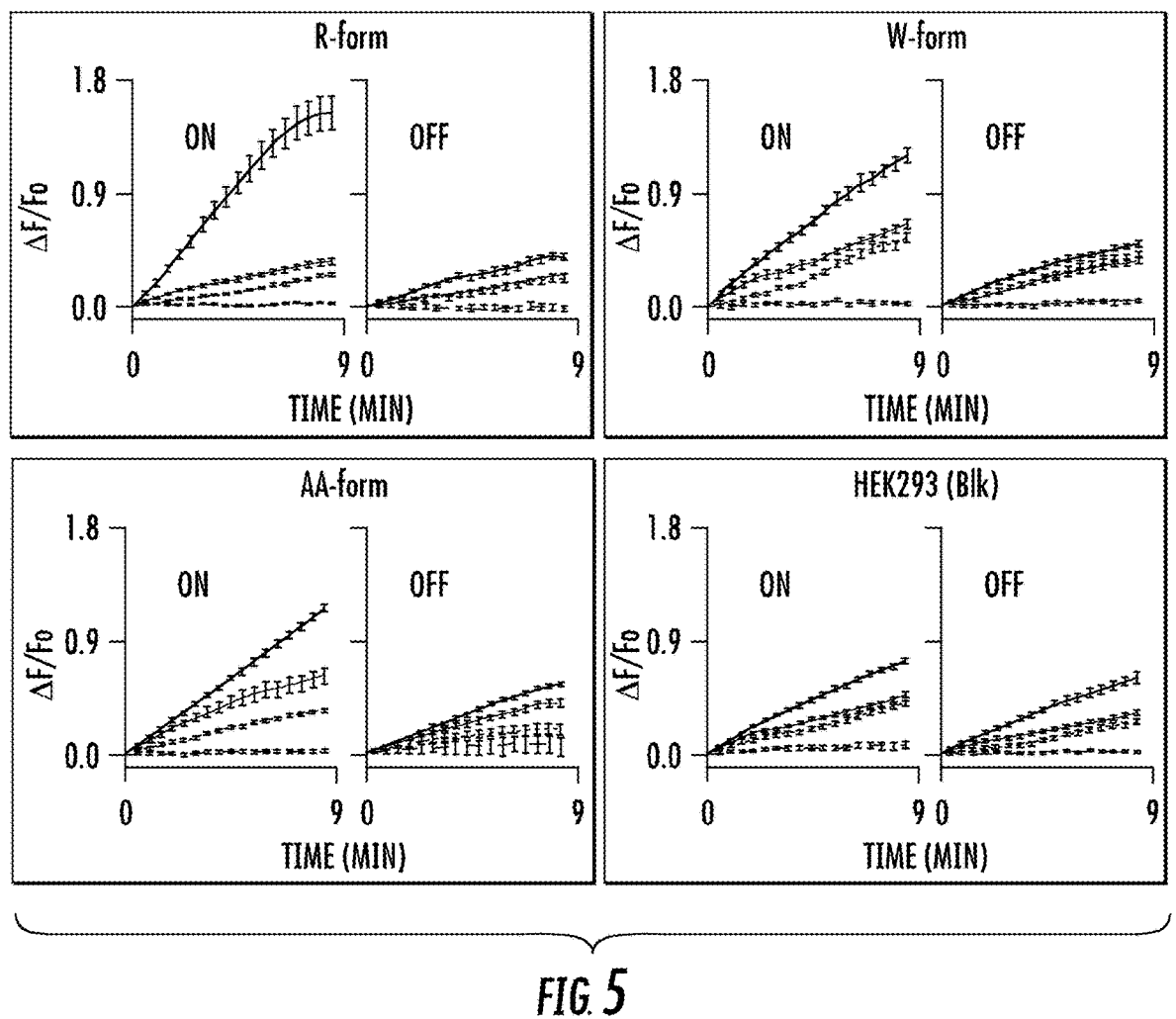
FIG. 5 illustrates the time courses of Zimpry-1 fluorescence in response to the addition of zinc at 0, 5, 19 or 283 nM. The fluorescence response were measured in stable expression HEK293 cells with or without induction of the R and W form as indicated. Blk is a negative control using parental HEK293 cells with no ZnT8 over-expression.
Figure 6:
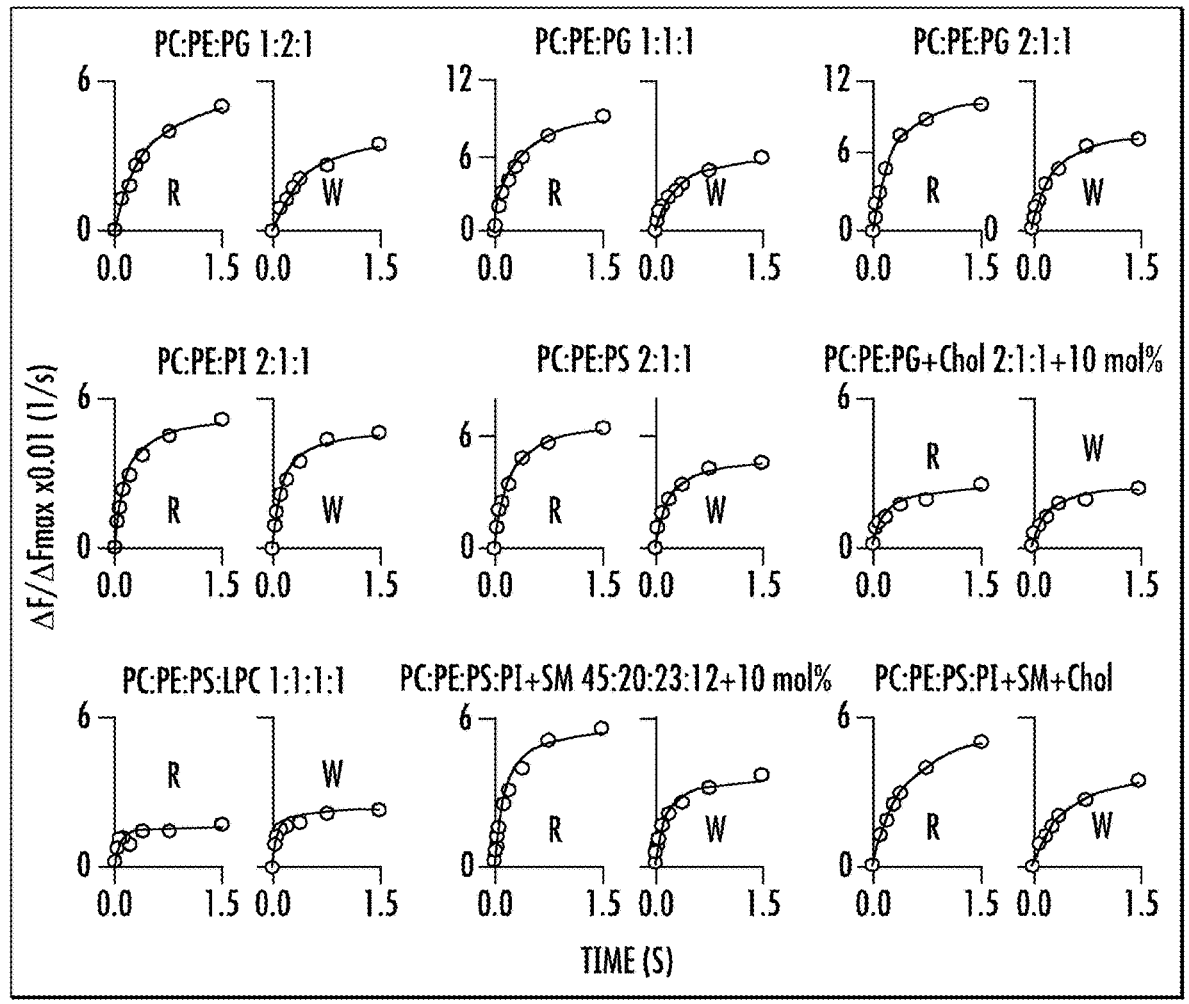
FIG. 6 illustrates steady state kinetics of the R and W form in reconstituted proteoliposomes with defined compositions as indicated.

Significant vesicular zinc accumulation observed in Blk (FIG. 5) was attributed to endogenous zinc transport activities of a multitude of zinc efflux and uptake transporters. The high background fluorescence signal, and a lack of a precise control over subcellular loading of the zinc indicator limited the potential for a quantitative comparison of ZnT8 variants. To directly compare zinc transport activities and determine which step(s) in the transport reaction cycle might be affected by the risk allele, we set out to purify ZnT8 variants and to develop functional reconstitution for in-depth kinetic analysis. Homology modeling of human ZnT8 based on the crystal structure of the bacterial zinc transporter YiiP suggested that ZnT8 forms a unique Y-shaped homodimer in which two transmembrane domains (TMDs) splay out in the membrane (FIG. 2A). Lipid molecules are expected to play an essential stabilizing role by filling the void space between two TMDs. Accordingly, we minimized ZnT8 delipidation in the purification process by coupling affinity purification to liposome reconstitution. The proteins eluted from metal affinity resins contained a major ZnT8 species as shown by SDS-PAGE (FIG. 2B). Most protein contaminants were not reconstituted, thus could be separated from reconstituted ZnT8 in proteoliposomes by ultracentrifugation. Re-solubilization of proteoliposomes yielded a mostly pure protein species with slightly reduced mobility on SDS-PAGE (FIG. 2B). The molecular identities of protein bands before and after reconstitution were confirmed by western blotting using antibodies to a N-terminal epitope in ZnT8 and the C-terminal His-tag, respectively (FIG. 2B).

Figure 2C:
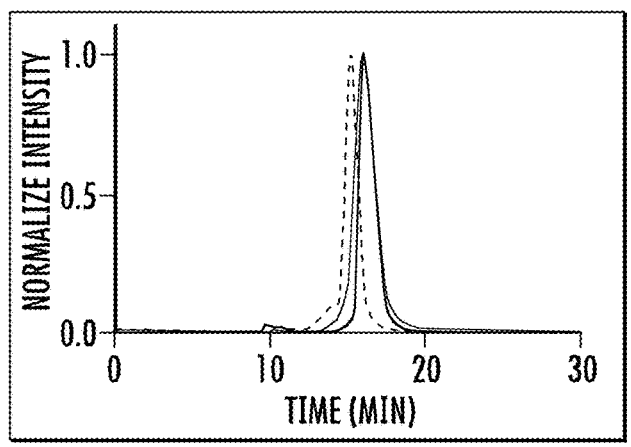

The purified ZnT8 variants were further assessed for protein folding by size-exclusion HPLC analysis. Despite having a predicted molar absorptivity of 41535 $M^{-1}$ $cm^{-1}$, the purified ZnT8 was nearly UV silent, probably due to the high lipid content in the detergent micelles. To detect ZnT8 elution, we labeled the purified sample with a thiol-specific fluorescent probe, fluorescein-5-maleimide, and then monitored labeled-ZnT8 by fluorescent and UV detection in tandem. Size-exclusion HPLC analysis of DDM-solubilized proteoliposomes revealed a single fluorescent peak. SDS-PAGE analysis of the peak fraction with coomassie stain confirmed the presence of purified ZnT8 (FIG. 2B). HPLC re-run of the peak fraction yielded single, mono-dispersed peaks by both fluorescent and UV detections (FIG. 2C). The apparent molecular weight of the purified ZnT8 was estimated to be ~120 kDa, in agreement with a dimeric assembly of two 36.5 KDa monomers with bound lipids and detergents. Compared with GFP-tagged ZnT8 in detergent crude extract, the purified ZnT8 without a GFP-tag was slightly right-shifted as a result of protein size difference (FIG. 2C). The peak profile, however, remained essentially unchanged between the purified ZnT8 and unpurified ZnT8-GFP, indicating that ZnT8 retained a native fold after purification, reconstitution and re-solubilization. For clarity, only the HPLC chromatogram of the R-form is shown, as the profiles of the W- and AA-form were essentially identical.

Kinetic Difference of ZnT8 Variants in Reconstituted Biomimetic Membranes.

Figure 3A:
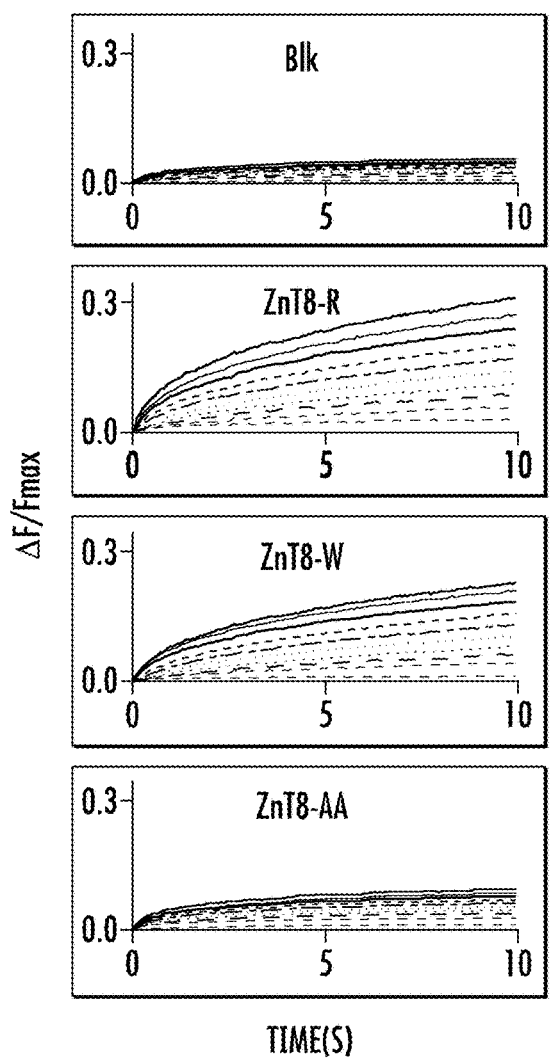
FIG. 3A-3B illustrates the kinetic analysis of ZnT8 variants.
Figure 3B:
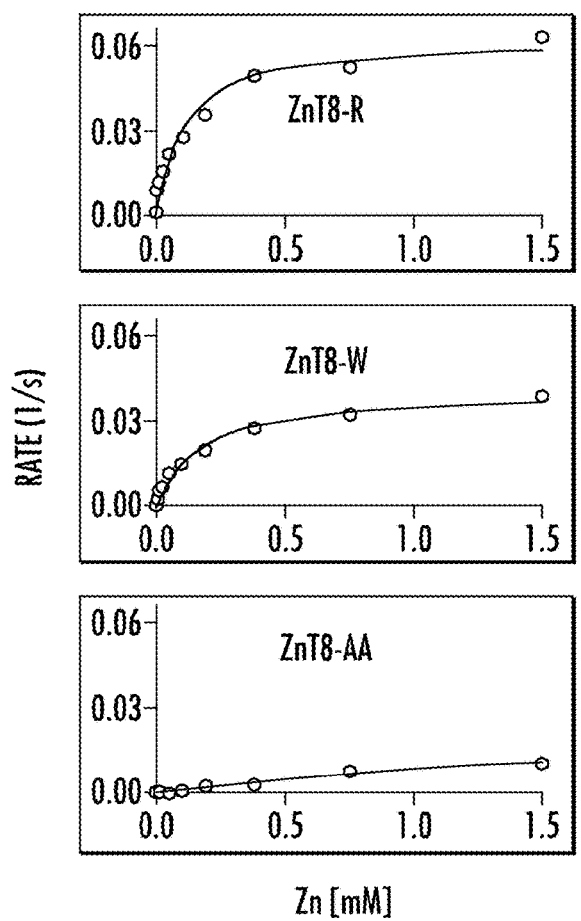

Zinc transport by ZnT8 is thought to be a two-step process, initiated by zinc binding to a transport-site followed by a protein conformational change that moves the bound zinc ion across the membrane barrier. This kinetic process was characterized for bacterial zinc transporters in reconstituted proteoliposomes (Chao Y & Fu D (2004) *J Biol Chem* 279, 12043-12050). However, reconstitution of human ZnT8 variants either caused large vesicle leakage when *E. coli* polar lipid extract was used, or yielded no detectable transport activity when bovine liver polar lipid extract was used. To achieve low background leakage and high transport activity, we used a mix of synthetic Dioleoylphosphatidyl-Choline (DOPC), 1,2-di-(9Z-octadecenoyl)-sn-glycero-3-phosphoethanolamine (DOPE), 1,2-dioleoyl-sn-glycero-3-phospho-L-serine (DOPS) and pure soy phosphatidylinositol (PI) at a ratio (45:20:23:12) that mimicked the phospholipid composition of insulin secretory granules of rat pancreatic beta cells (INS-1 832/13 cells). ZnT8-mediated zinc transport was monitored by Fuozin-3, a membrane impermeant fluorescent zinc indicator encapsulated in proteoliposomes. ZnT8-mediated zinc influx was about 5-10 fold higher than the background leakage measured in liposomes that were prepared without protein incorporation (FIG. 3A). The R- or W-form responded to an increasing extravesicular zinc concentration with a hyperbolic increase of the initial rate of Fluozin-3 fluorescence change (FIG. 3A). Least squares fitting of the steady-state kinetics to Michaelis-Menten equation indicated that the rate of zinc transport (Vmax) for the high-risk R-form was 51% faster, accompanied by a small decease of Km (FIG. 3B, Table-1). The Vmax/Km value of the R-form, which is a measure of zinc transport efficacy, was 2.4 fold higher as compared to that of the W-form.

The site of R-to-W substitution in human ZnT8 is predicted to be in the vicinity of a cytosolic zinc-binding site in CTD (FIG. 2A). This site is more than 50 angstroms away from the zinc transport-site in TMD. Mutating the cytosolic zinc-binding site of YiiP was found to impair a CTD conformational change, leading to an allosteric down-regulation of the zinc transport activity (17). The increased zinc transport activity of the high-risk R-form is consistent with a functional enhancement via allosteric over-stimulation. By comparison, the double Ala-substitution to the transport-site in TMD is predicted to impact zinc transport directly, in agreement with a 24-fold Km increase and 59-fold Vmax/Km decrease as compared to the corresponding kinetic parameters of the R-form. Previous work showed that Ala-substitution of highly conserved zinc binding residues abolished transport activity of a homologous human ZnT5 and a bacterial YiiP. Although the AA-form apparently remained functional at a reduced level, the initial rate of zinc transport seemed linear with a zinc concentration up to 1.5 mM (FIG. 3B), suggesting a possible nonspecific zinc leakage when the specific transport-site was disrupted by a targeted mutation. Thus, the Vmax value of the AA-form ($0.028\pm0.008$ $s^{-1}$) defined an upper bound non-specific leakage contributing to the kinetic measurement of human ZnT8 variants in reconstituted proteoliposomes.

Functional Modulation of Human ZnT8 Variants by Lipids.

Figure 4:
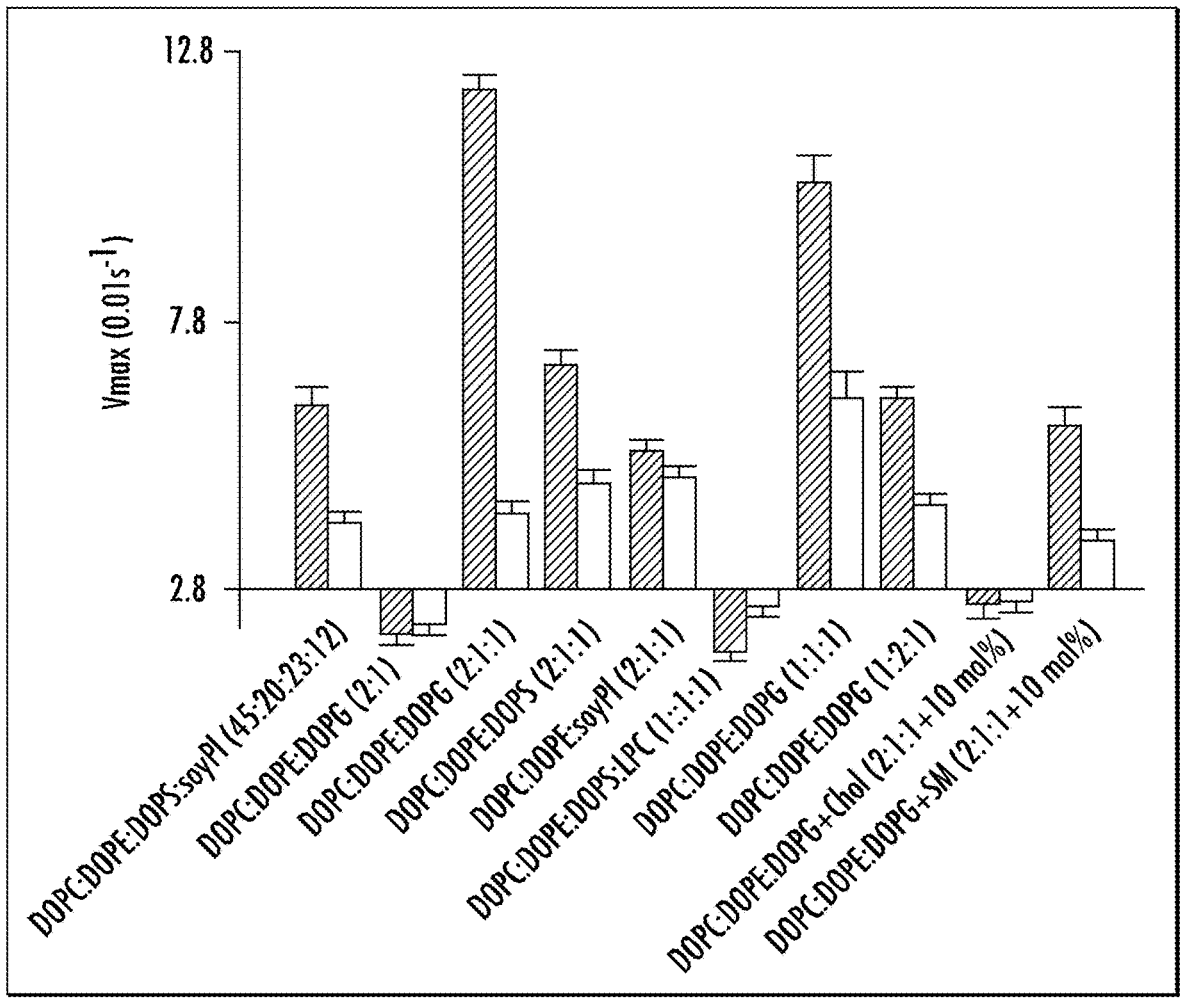
FIG. 4 illustrates the functional regulation of ZnT8 by lipids.

During replenishment of insulin granules following glucose stimulated insulin secretion, ZnT8 is trafficked with insulin granule biogenesis en route from the endoplasmic reticulum through Golgi networks to insulin secretory granules. The intracellular trafficking process exposes ZnT8 to a dynamic lipid composition as the membranes undergo curvature formation, granule budding and exocytotic fusion. The remodeling of insulin granule membranes results in enrichments of anionic phosphatidylinositol (PI), phosphatidylserine (PS), non-bilayer lysophosphatidylcholine (LPC) and cholesterol. We further investigated the functional difference between ZnT8 variants under the influence of three major classes of lipids in insulin granules: anionic phospholipids, non-bilayer phospholipids and cholesterol. In almost all mammalian cells, PC accounts for 50% of total cellular phospholipids. PE is the second most abundant phospholipid in mammalian membranes, contributing 20-30% of total phospholipid content. We therefore used a 2:1 mixture of DOPC and DOPE to form a minimal biomimetic membrane and then examined the effect of adding a third anionic phospholipid. The efficiencies of ZnT8 reconstitution for both variants as well as Fluozin-3 vesicular encapsulation remained approximately the same for the following lipid compositions, DOPC:DOPE (2:1), DOPC:DOPE:DOPG (2:1:1), DOPC:DOPE:DOPS (2:1:1) and DOPC:DOPE: soyPI (2:1:1). The zinc transport activities of both variants in the DOPC:DOPE (2:1) proteoliposomes were severely reduced below the Vmax level of the AA-form at $2.8\times10^{-2}$ $s^{-1}$ (FIG. 4). DOPG, DOPS or soyPI increased Vmax by 6.1, 3.5 or 2.7 fold for the R-form, and 2.0, 2.3, or 2.3 fold for the W-form (Table-1). All three anionic phospholipids, regardless of the exact chemical nature of the headgroup, activated zinc transport. Of note, the Vmax values of the R-form were consistently larger than the W-form under all conditions of anionic lipid stimulation (FIG. 4). The zinc transport-site in the homolog model is situated in the outer leaflet of the lipid bilayer and partially accessible to interactions with surrounding lipid headgroups (FIG. 2A). DOPS and soyPI, both abundantly found in the insulin granule membranes, seemed to facilitate zinc binding as suggested by a modest decrease of Km values (Table 1). DOPG is not a native anionic lipid in insulin granules with slightly increased Km values for both the R- and W-form.

TABLE 1

Summary of kinetic parameters

| | ZnT8 Variant | | | |
| --- | --- | --- | --- | --- |
| | R325 | | W325 | |
| Lipid compositions | Vmax (0.01s$^{-1}$) | Km ($\mu$M) | Vmax (0.01s$^{-1}$) | Km ($\mu$M) |
| DOPC:DOPE:DOPS:soyPI (45:20:23:12) | 6.22 ± 0.38 | 103.1 ± 22.2 | 4.07 ± 0.19 | 162.2 ± 24.4 |
| DOPC:DOPE (2:1) | 2.00 ± 0.22 | 205.4 ± 70.0 | 2.15 ± 0.15 | 169.2 ± 36.8 |
| DOPC:DOPE:DOPG (2:1:1) | 12.10 ± 0.31 | 252.9 ± 18.8 | 4.22 ± 0.22 | 218.4 ± 40.0 |
| DOPC:DOPE:DOPS (2:1:1) | 6.99 ± 0.28 | 165.5 ± 21.1 | 4.97 ± 0.26 | 159.2 ± 30.0 |
| DOPC:DOPE:soyPI (2:1:1) | 5.39 ± 0.21 | 131.0 ± 17.7 | 4.95 ± 0.16 | 125.2 ± 14.3 |
| DOPC:DOPE:DOPS:LPC (1:1:1:1) | 1.69 ± 0.17 | 33.0 ± 17.0 | 2.47 ± 0.18 | 52.3 ± 16.4 |
| DOPC:DOPE:DOPG (1:1:1) | 10.39 ± 0.53 | 259.7 ± 36.3 | 6.39 ± 0.47 | 219.3 ± 46.8 |
| DOPC:DOPE:DOPG (1:2:1) | 6.39 ± 0.16 | 418.2 ± 25.4 | 4.36 ± 0.22 | 416.5 ± 44.9 |
| DOPC:DOPE:DOPS:soyPI + SM (45:20:23:12 + 10 mol %) | 5.84 ± 0.37 | 125.6 ± 25.2 | 3.73 ± 0.24 | 104.8 ± 24.3 |
| DOPC:DOPE:DOPG + cholesterol (2:1:1 + 10 mol %) | 2.57 ± 0.32 | 134.0 ± 56.1 | 2.59 ± 0.24 | 160.3 ± 47.3 |
| DOPC:DOPE:DOPS + cholesterol (2:1:1 + 10 mol %) | ND | ND | ND | ND |
| DOPC:DOPE:LPC:DOPS + cholesterol (1:1:1:1 + 10 mol %) | ND | ND | ND | ND |

Next we examined the effects of two non-bilayer phospholipids, namely the invert conical LPC and conical DOPE. These non-cylindrical phospholipids alone do not form lipid bilayers, but can be stabilized in the bilayer structure by the presence of 20-50% cylindrical phospholipids (DOPC, DOPS and DOPG). Adding LPC to 25% or increasing the DOPE concentration in reconstitution mixture did not affect the efficacies of ZnT8 insertion and Fuozin-3 encapsulation, but background zinc leakage slightly increased due to increased bilayer deformation. LPC (Lysophosphatidylcholine, lysoPC) in reconstituted DOPC:DOPE:DOPS:LPC (1:1:1:1) proteoliposomes reduced the Vmax value of both ZnT8 variants below the reference level of the AA-form (FIG. 4). Interestingly, LPC also significantly reduced the Km values of both ZnT8 variants (Table-1). The apparent tightening of zinc binding seemed to impede the transmembrane crossing of bound zinc, resulting in a marked decrease of Vmax for both ZnT8 variants. LPC is highly enriched in insulin granules, accounting for 20% of total granule lipids. When inserted into the lipid bilayer, the cone-shaped LPC introduced positive curvature, and the ensuing redistribution of the bilayer lateral pressure might in turn inhibited ZnT8. In contrast, DOPE in the lipid bilayer promoted negative curvature, and increasing the concentration of DOPE in DOPC:DOPE:DOPG proteoliposomes from a ratio of 2:1:1 to 1:1:1 and 1:2:1 had modest effects on the W-form, but progressively reduced the Vmax of the R-form. Our experiments suggested that significant bilayer curvature changes, either in a positive or negative direction, inhibited zinc transport activity to various degrees.

The third highly enriched lipid class in insulin granule is cholesterol. The compact and conical cholesterol molecules can fit into the void space between fatty acid chains, increasing packing density and bending rigidity of the lipid bilayer. A cholesterol composition probably in the range of 40-50 mol % is required for normal insulin secretion. Many residential proteins in the insulin granule have high affinity to cholesterol, likely lowing the actual cholesterol level in the granular membrane. To examine the effect of cholesterol on ZnT8 transport activity, we added 10 mol % cholesterol to proteoliposomes made with DOPC:DOPE:DOPG (2:1:1), DOPC:DOPE:DOPS (2:1:1) or DOPE:DOPC:LPC:DOPS (1:1:1:1). The incorporation of cholesterol into proteoliposomes did not affect ZnT8 reconstitution and Fuozin-3 encapsulation, but invariably reduced the transport activities of both ZnT8 variants below the reference level of the AA-form (Table-1). The inhibitory effect of cholesterol explained a complete loss of ZnT8 transport activity in bovine liver polar lipid extract that contained 10 mol % cholesterol.

Recent human population genetics has identified rare loss-of-function ZnT8 variants that confer strong protective effects against T2D. This discovery validated human ZnT8 as an antidiabetic drug target. The actual target of therapeutic interventions is the common R325 risk allele in the general population. The translation of rare loss-of-function alleles to therapeutic inhibition of the common risk variant is questioned by the possibility of a bell-shaped relationship between ZnT8 activity and T2D risk. In this work, we developed quantitative analysis of human ZnT8 variants and characterized regulatory effects of major lipid components found in insulin secretory granules. Our experiments showed that the transport activity of human ZnT8 is sensitive to functional modulations by three classes of lipids rich in insulin secretory granules: the anionic lipids activate whereas LPC and cholesterol strongly inhibit both ZnT8 variants. The high-risk R325 variant is consistently more active than the low-risk W325 variant under all experimental conditions favoring transport competence (FIG. 4). The observed hyperactivity of the high-risk R325 variant mirrors a causal relationship of loss-of-function human mutants to lower T2D risk. Our results suggest that ZnT8 activity is linearly correlated with T2D risk from a mild ZnT8 polymorphic variant to penetrant loss-of-function mutants. The association of the human high-risk R325 variant with ZnT8 hyperactivity suggests that the over-stimulated R325 variant may be targeted for inhibition to reduce T2D risk in the general population.

Kinetic analysis of human ZnT8 variants in various biomimetic membranes of defined lipid compositions provides insights into functional dynamics of human ZnT8 in pancreatic beta cells. The inhibitory LPC and cholesterol are both non-bilayer lipids. Their actual concentrations in the insulin granule membrane are highly dynamic, depending on the partitioning between residential lipid-binding proteins and the granular membrane. Rapid turnover of the secretory pathway is a basic functional requirement for pancreatic beta cells to maintain homeostatic abundance of insulin granules. During this process, ZnT8 is trafficked with insulin granule biogenesis, thus encounters drastically different lipid compositions from ER to matured insulin secretory granules. ZnT8 is commonly assumed to pump cytosolic zinc into insulin granules against a steep concentration gradient. However, the abundant presence of strong inhibitory lipids in insulin granules argues for a functional down-regulation of granular ZnT8. Secretory granules store an exceptionally high level of zinc in 10 to 30 mM range, while the free zinc concentration in the cytoplasm is kept around a homeostatic set point below nM. The inactivation of granular ZnT8 may help reducing zinc backflow out of the zinc-enriched granules. The lipid compositions in the early secretory pathway seem more permissive for ZnT8-mediated zinc accumulation. Proinsulin is synthesized in ER and loaded with zinc during the transit from ER to cis-Golgi networks. Sorting zinc-bound (pro)insulin into secretory granules could be an alternative mechanism of granular zinc enrichment if ZnT8 is indeed inhibited in the late secretory pathway. Functional studies of ZnT8 in live beta cells still await enabling technologies to track spatiotemporal dynamics of lipid compositions, subcellular ZnT8 localization and zinc concentrations at the same time.

Embodiments of the disclosure concern methods and/or compositions for treating and/or preventing diabetes including Type-1 or Type-2 diabetes. In certain embodiments, the level to which a drug inhibits ZnT8 activity or expression may be any level so long as it provides amelioration of at least one symptom of diabetes. The level of ZnT8 activity may decrease by at least 2, 3, 4, 5, 10, 25, 50, 100, 1000, or more fold expression compared to the level of a reference, in at least some cases. An individual may monitor ZnT8 expression/activity using standard methods in the art, such as northern assays or quantitative PCR, for example.

An individual known to have diabetes, suspected of having diabetes, or at risk for having diabetes may be provided an effective amount of an inhibitor of ZnT8 activity and/or expression, including lipids. Those at risk for diabetes may be those individuals having one or more genetic factors, may be of advancing age, and/or may have a family history, for example.

In particular embodiments of the disclosure, an individual is given an agent for diabetes therapy in addition to the one or more inhibitors of ZnT8. Such additional therapy may include pharmaceutical agents that are commercially available, for example. When combination therapy is employed with one or more inhibitors of ZnT8, the additional therapy may be given prior to, at the same time as, and/or subsequent to the inducer of ZnT8.

Certain methods of the disclosure provide for methods of diagnosing diabetes prior to the therapeutic methods of the disclosure, and such diagnosis may occur by any methods or means, including at least genetic marker assay.

Pharmaceutical Preparations.

Pharmaceutical compositions of the present invention comprise an effective amount of one or more inhibitors of ZnT8 such as lysophospatidylcholine, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one inhibitor of expression and/or activity of ZnT8 or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The inhibitor of the activity and/or expression of ZnT8 may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art.

The inhibitor of activity and/or expression of ZnT8 (including lysophoshatidylcholine) may be provided to the individual in need thereof by dietary ingesting one or more comestibles that comprise the inhibitor, such as herbs, berries, and/or fruits.

The inhibitor of the activity and or expression of ZnT8 may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with cells of the pancreas, or other mammalian cells such as human cells, for example. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include inhibition of activity and/or expression of ZnT8, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skilled in the art would be familiar with the range of techniques that can be employed for dispersing a composition in a lipid vehicle. For example, the inhibitor of activity or expression of ZnT8 may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations. In one embodiment of the present disclosure, the inhibitors of activity and/or expression of ZnT8, or variants thereof, are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations.

In further embodiments, inducer of expression of ZnT8 may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations.

In other preferred embodiments of the invention, the active compound inhibitor of activity and/or expression of ZnT8. or variants thereof, may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

EXAMPLES/METHODS

Expression Constructs.

The human ZnT8 isoform-2 cDNA (NM_001172814.1) housed in a pCMV6-entry vector (OriGene Technologies) was shuttled into a mammalian expression vector pCMV6-AC-GFP with a modified turboGFP tag appended to the C-terminus. The resulting (pZnT8-GFP) was transiently expressed in HEK293 cells by Lipofectamine transfection according to manufacturer's instructions (Thermo Fisher). The human ZnT8 cDNA insert was further subcloned into a pcDNA5/FRT/TO expression vector that used a tetracycline-inducible, hybrid human cytomegalovirus (CMV)/TetO$_2$ promoter to control ZnT8 expression (Life technologies). A hexahistidine tag was added to the C-terminus to facilitate affinity purification. The resulting His-tagged ZnT8 expression construct (the R-form), pZnT8-His, was also mutated to generated the W-form (R325W mutation) and AA-from (H220A, D224A double mutation) using Q5 Site-Directed Mutagenesis (New England Biolabs). All constructs were confirmed by double strand DNA sequencing.

Stable Cell Lines.

Expression cell lines with stable integration of various ZnT8 variants were generated by co-transfection of pZnT8-His and pOG44 at 1:9 ratio into an Flp-In-T-Rex-HEK293 host cell line (Life Technologies). This cell line constitutively expressed Tet repressor and contained a single integrated Flp Recombination Target (FRT) site. The expression of an Flp recombinase encoded in pOG44 mediated genomic integration of the pZnT8-His construct via homologous recombination at specific FRT sites. The integration also activated the expression of a hygromycin resistant gene, allowing antibiotic selection of stable expression cell lines. Since all of the hygromycin resistant foci were isogenic, polyclonal stable cell lines were pooled and used for all experiments as described below. A separate cell line (Blk) with stable integration of the empty pcDNA5/FRT/TO vector was generated in parallel as a negative control for immunofluorescence imaging and vesicular zinc uptake experiments.

ZnT8 Expression.

Flp-In, T-REx-HEK293 cells stably expressing His-tagged ZnT8 variants were grown in Dulbecco's modified Eagle's medium supplemented with 10% tetracycline-reduced fetal bovine serum and 100 g/ml hygromycin B in 95% air, 5% carbon dioxides at 37° C. Early-passage cells (n<10) with a >95% viability were counted (typically at $1 \times 10^7$ cells/ml), seeded at an appropriate density (see below) suited for different experiments on poly-Lys coated surfaces. When cells were grown exponentially to approximately 70% confluent in monolayers, doxycycline was added to 1 μg/ml to induce ZnT8 expression. Experiments were performed 18-24 hours after expression induction.

Immunofluorescence.

For visualization of His-tagged ZnT8 expression, stable expression cells were grown on coverslips with or without doxycycline induction. Cells at 50% confluence were fixed with 4% paraformaldehyde, treated with a primary mouse monoclonal antibody recognizing the C-terminal His-tag (Abcam, cat. #ab5000, dilution 1:100), followed by a goat-anti-mouse secondary antibody conjugated with Alexa Fluor-594 (Thermo Fisher, cat. #A11005, dilution 1:200). Nuclei were counterstained with DAPI. For visualization of vesicular zinc accumulation, cells were grown on coverslips in glass bottom microwell dishes. Induced cells at 50% confluence were labeled by 5 uM Zinpyr-1 added to the culture medium. 30 min after incubation at 37° C., cells were washed free of excess Zinpyr-1 with Dulbecco's PBS, and then exposed to 100 uM zinc added extracellularly. Cells were then imaged using a Zeiss LSM 700 inverted confocal microscope with a 63× oil objective. Alexa Fluor-594, DAPI and Zinpyr-1 fluorescence were excited by three separate laser lines (561, 405 and 488 nm), and monitored at respective emission wavelength ranges under the control of Zen software.

Flow Cytometry.

Stable expression cells were grown in 6-well cell culture plates, induced at 70% confluence, and then labeled with 5 uM Zinpry-1 as described above. The labeled cells were washed free of excess Zinpry-1 with Hanks' Balanced Salt Solution (HBSS) with glucose, exposed to 100 uM extracellular zinc at room temperature for 30 min. Then, cells were trypsinized, resuspended in ice-chilled HBSS at a density of $1 \times 10^6$ cells/ml, and kept on ice until running through a flow cytometer. Flow cytometric analyses of vesicular zinc accumulation were performed on a MoFlo XDP cell sorter (Beckman Coulter) equipped with a 488 nm laser. Data were collected on the forward scatter, side scatter, and 525 nm fluorescence channel. More than 99% of scattering events belonged to a singlet cell population with 98% cell viability based on propidium iodide staining analysis. Zinpyr-1 fluorescence measured from ~13,000 live cells were used to calculate the mean level of vesicular zinc accumulation for each ZnT8 variant.

Vesicular Zinc Uptake.

An uptake buffer with a free zinc concentration ranging from 4.4 to 283 nM was prepared by adding 0.3-1.7 mM $ZnSO_4$, 1 mM ADA, 1 mM EGTA and 1 uM pyrithione to an assay buffer (100 mM NaCl, 20 mM HEPES, I mM TECP, pH 7.0). The free zinc concentration in the ADA-EGTA dual buffering system was calculated using maxchelator (maxchelator.stanford.edu). Induced cells were loaded with Zinpry-1, trypsinized, resuspended in an ice-chilled plain uptake buffer with no $ZnSO_4$ added. Cells with the expression of each ZnT8 variant or the empty vector were counted, adjusted to a density of $4 \times 10^6$ cells/ml, and dispensed in 50-□l aliquots to a clear-bottom 96-well microplate (Greiner bio-one). Initial Zinpry-1 fluorescence ($F_0$) was recorded from the bottom on a Flexstation-3 microplate reader (Molecular dynamics), and then zinc-uptakes were initiated by adding 50 ul uptake buffers with 2× free zinc concentrations to each well. The Zinpry-1 fluorescence increases in response to various free zinc concentrations were recorded at 15° C. in the kinetic mode of Flexstation over a time course of 10 min and normalized to Zinpyr-1 loading ($F_0$). The fluorescence responses reached a linear phase in 2 min after the uptake temperature approached equilibrium. The rates of zinc uptake were calculated by linear regression of the Zinpyr-1 signals from 2 to 10 min. All measurements were performed in 12 replicates, and fluorescence readings were obtained by averaging over 8-10 measurements that gave consistent results. Most aberrant measurements occurred in the first and last two columns of the microplate due to pipetting errors.

Purification and Reconstitution.

24 hour after induction, early-passage cells (passage number <10) at 90% confluence were scraped on ice and collected in the assay buffer supplemented with complete mini EDTA free protease cocktail tablets as specified by the manufacturer (Sigma). Cell suspension was homogenized by 40 passages through a high-shear fluid processor at 120 psi (Microfluidics), and then the membrane fraction was pelleted by ultracentrifugation at 258 k×g for 60 min. The membrane pellet was re-suspended in a solubilization buffer (assay buffer plus 25% glycerol). DDM was added to solubilize the membrane according to the weight of the membrane pellet at a DDM-to-membrane ratio of 1:5 (wt/wt). The membrane crude extract was cleared off debris by ultracentrifugation at 258 k×g for 15 min. The supernatant was applied to Talon affinity resins (GE Healthcare) and incubated at 8° C. on a rotary shaker for 45 min. The resin was then minimally washed by solubilization buffer supplemented with 25 mM imidazole, and then the immobilized ZnT8 variant was eluted by increasing the imidazole concentration to 250 mM. The molecular identity of the eluted ZnT8 variant was validated by western blotting using two antibodies to the C-terminal His-tag (Cell signaling Technology, cat. #2365S, catalog number, 1:1000 dilution) and to a linear peptide epitope (Proteintech, cat. #16169-I-AP, 1:500 dilution), respectively. The purity of the eluted proteins was assessed by SDS-PAGE with imperial protein staining (Thermo Scientific). Preformed liposomes with a defined lipid composition as indicated were prepared by mixing stock solutions of lipids in chloroform. The lipid mixture was dried under a stream of nitrogen gas, and traces of chloroform were removed by placing the lipids under vacuum overnight at room temperature. Dried lipids were rehydrated in a Pyrex borosilicate glass tube with assay buffer to a lipid concentration of 50 mg/ml, and then sonicated in a cup-horn sonicator at 100 W for 2 min (cycles of 10 son, 10 s off) in an ice-chilled water bath. The resulting liposome suspension was diluted with assay buffer to a final lipid concentration of 7.5 mg/ml with DDM added at a DDM/lipids ratio of 1:1 (wt/wt). The DDM-liposome mixture was incubated at room temperature on a rotary shaker for ~3 hours until a gel-like appearance occurred. Reconstitution of ZnT8 variants took place immediately after eluted from Talon resins by mixing a ZnT8 variant, or an equal volume of elution buffer, with DDM-destabilized preformed liposomes at an estimated protein-to-lipid wt/wt ratio of 1:200. The reconstitution mixture was incubated on a rotary shaker at 8° C. for 1 hr, then freshly prepared, methanol-washed polystyrene beads (Bio-Beads, SM-2, Bio-Rad) were added to the reconstitution mixture in a 60:1 wt/wt ratio to DDM. After incubation overnight at 8° C., the resulting proteoliposomes or liposomes (negative control) were separated from the detergent-soaked polystyrene beads, and pelleted by ultracentrifugation (258 k×g, 2 hr). The vesicle pellets were resuspended in 0.2 ml assay buffer with 200 □M Fluozin-3, subjected to 3 freeze-thaw cycles, followed by a 10 second sonication to complete dye encapsulation. The extravesicular Fluozin-3 was removed by washing vesicles with 3×25 ml assay buffer by three cycles of resuspending and ultracentrifugation (258 k×g, 0.5 hr).

Stopped-flow kinetics. Experiments were performed at 8° C. on a SFM-3000 stopped-flow apparatus (Bio-logic). Proteoliposome or liposome samples and an assay buffer containing varying concentrations of $ZnSO_4$ as indicated were loaded into two separate mixing syringes. Zinc influx reactions were initiated by pushing 101 ul fresh reactants at a 1:1 ratio into a mixing chamber at a flow rate of 10 ml/s. The reactants were excited at 490 nm, and emissions were monitored at 525 nm using a 10 nm bandpass cut-off filter. Kinetic traces were recorded over a time course of 10 seconds with instrument offset and gain kept constant for all the experiments. All traces were the cumulative average of 5 successive recordings. Liposome traces were collected as baselines and subtracted from proteoliposome traces to yield net fluorescence changes $\Delta F$. $\Delta F/\Delta F_{max}$ was obtained by normalizing $\Delta F$ to the maximum proteoliposome response elicited by an assay buffer containing 3 mM $ZnSO_4$ plus 2%

β-OG. The initial rate of zinc influx was obtained by linear regression of data points (t<1 s) in the quasi-linear phase of the initial fluorescence rise. Concentration dependence data were analyzed by least squares fits of the initial transport rate to a hyperbola defined by vi=Vmax·M/(M+Km), where M represents the zinc ion concentration, Vmax is the maximum initial transport rate when the rate of transport approaches to a quasi-stationary state, and Km is the Michaelis-Menten constant. Fits of experimental data were preformed using the data analysis software SIGMAPLOT (SPSS Inc., Chicago, Ill.).

Homology Modeling.

The protein sequences of the R-allele of human ZnT8 isoform-2 and *E. coli* zinc transporter YiiP were aligned using MODELLER 9.16 (https://salilab.org/modeller/). The alignment was imported into Swiss model (http://swissmodel.expasy.org) to generate a homolog model of ZnT8 using the crystal structure of YiiP at 2.9-angstrom resolution as a template (pdb #3H90). The graphic representation of the resulted model was prepared using the program PyMol (Delano Scientific).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of identifying a drug to treat diabetes in a subject comprising the steps of:
    (a) providing a proteoliposome comprising a zinc transporter ZnT8, or functional part thereof;
    (b) administering an agent to the proteoliposome forming a treated sample;
    (c) measuring the activity of the zinc transporter ZnT8 in the treated sample to obtain a first activity measurement and comparing the first activity measurement to a second activity measurement of a reference; and
    (d) identifying the drug when the first activity measurement is lower than the second activity measurement.

2. The method of claim 1 wherein the reference is the proteoliposome comprising a ZnT8 transporter or functional part thereof substantially free of the agent.

3. The method of claim 1 wherein the activity of zinc transporter ZnT8 is the rate of zinc transport efficiency.

4. The method of claim 1 wherein the first measurement is from 1.5 to 5 fold lower than the second measurement.

5. The method of claim 3 wherein the rate of zinc transport efficiency is based on a Vmax/Km value using stopped-flow kinetics.

6. A method of identifying a drug to treat diabetes in a subject comprising the steps of:
    (a) providing a first sample that expresses a zinc transporter ZnT8, or functional part thereof;
    (b) administering an agent to the first sample forming a treated sample;
    (c) measuring the activity of the zinc transporter ZnT8 in the treated sample to obtain a first activity measurement and comparing the first activity measurement to a second activity measurement of a reference; and
    (d) identifying the drug when the first activity measurement is lower than the second activity measurement.

7. The method of claim 6 wherein the zinc transporter is the nonsynonymous variant of human ZnT8 (R325W).

8. The method of claim 6 wherein the first sample is in vitro human cells.

9. The method of claim 6 wherein the first sample is a biological sample obtained from a subject.

10. The method of claim 6 wherein the activity of the zinc transporter ZnT8 is measured by intracellular zinc accumulation in the sample.

11. The method of claim 6 wherein the activity of the zinc transporter ZnT8 is measured by a rate of zinc transport efficacy.

12. The method of claim 11 wherein the first activity measurement is from 1.5 to 5 fold lower than the second activity measurement.

13. The method of claim 12 wherein the rate of zinc transport efficiency is based on a Vmax/Km value using stopped-flow kinetics.

14. The method of claim 6 wherein the reference is the first sample substantially free of agent.

15. The method of claim 6 wherein the zinc transporter ZnT8 is a human zinc transporter ZnT8.

16. The method of claim 6 wherein the first sample is HEK293 cells.

17. The method of claim 16 wherein the ZnT8 is a His-tagged ZnT8.

18. The method of claim 17 wherein the HEK293 cells stably express the His-tagged ZnT8.

19. The method of claim 6, wherein the agent is selected from the group comprising an antibody, portion of an antibody, nucleic acid, peptide, protein, chemical, or combination thereof.

20. The method of claim 19, wherein the agent is a chemical.

* * * * *